United States Patent
Valamehr et al.

(10) Patent No.: US 12,122,846 B2
(45) Date of Patent: *Oct. 22, 2024

(54) CHIMERIC ANTIGEN RECEPTOR FOR TUMOR TARGETING

(71) Applicants: FATE THERAPEUTICS, INC., San Diego, CA (US); ONO PHARMACEUTICAL CO., LTD., Osaka (JP)

(72) Inventors: Bahram Valamehr, San Diego, CA (US); Tom Tong Lee, San Diego, CA (US); Martin Hosking, San Diego, CA (US); Susumu Yamamoto, Osaka (JP); Tatsuo Maeda, Osaka (JP)

(73) Assignees: FATE THERAPEUTICS, INC., San Diego, CA (US); ONO PHARMACEUTICAL CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/346,130

(22) Filed: Jun. 30, 2023

(65) Prior Publication Data
US 2024/0002532 A1   Jan. 4, 2024

Related U.S. Application Data

(63) Continuation of application No. PCT/US2023/065537, filed on Apr. 7, 2023.
(Continued)

(51) Int. Cl.
C07K 16/32 (2006.01)
C07K 14/705 (2006.01)
C07K 14/725 (2006.01)

(52) U.S. Cl.
CPC .......... *C07K 16/32* (2013.01); *C07K 14/7051* (2013.01); *C07K 14/70521* (2013.01);
(Continued)

(58) Field of Classification Search
None
See application file for complete search history.

(56) References Cited

U.S. PATENT DOCUMENTS 6,140,081 A   10/2000   Barbas
6,352,694 B1   3/2002   June et al.
(Continued)

FOREIGN PATENT DOCUMENTS

CN   112391414 A   2/2021
WO   WO 1998/053058 A1   11/1998
(Continued)

OTHER PUBLICATIONS

Stock et al. Optimizing Manufacturing Protocols of Chimeric Antigen Receptor T Cells for Improved Anticancer Immunotherapy. Int. J. Mol. Sci. 2019, 20, 6223. (Year: 2019).*
(Continued)

*Primary Examiner* — Daniel E Kolker
*Assistant Examiner* — Hilary Ann Petrash
(74) *Attorney, Agent, or Firm* — Greenberg Traurig, LLP

(57) ABSTRACT

Provided are chimeric antigen receptors (CAR) specific to a selected tumor antigen. Also provided are structure designs and function profiles of provided CAR candidates.

16 Claims, 11 Drawing Sheets

Specification includes a Sequence Listing.

Related U.S. Application Data

(60) Provisional application No. 63/329,287, filed on Apr. 8, 2022.

(52) U.S. Cl.
CPC ...... *C07K 2319/02* (2013.01); *C07K 2319/03* (2013.01); *C07K 2319/33* (2013.01)

(56) References Cited

U.S. PATENT DOCUMENTS

| | | |
|---|---|---|
| 6,453,242 B1 | 9/2002 | Eisenberg et al. |
| 6,534,261 B1 | 3/2003 | Cox et al. |
| 7,888,121 B2 | 2/2011 | Urnov et al. |
| 7,972,854 B2 | 7/2011 | Miller et al. |
| 8,409,577 B2 | 4/2013 | Thompson et al. |
| 9,447,194 B2 | 9/2016 | Jensen |
| 9,587,020 B2 | 3/2017 | Wu et al. |
| 10,927,346 B2 | 2/2021 | Valamehr et al. |
| 11,365,394 B2 | 6/2022 | Valamehr et al. |
| 11,981,747 B1* | 5/2024 | Kato ............... G01N 33/57415 |
| 2004/0101519 A1 | 5/2004 | June et al. |
| 2006/0034810 A1 | 2/2006 | Riley et al. |
| 2011/0145940 A1 | 6/2011 | Voytas et al. |
| 2014/0134142 A1 | 5/2014 | Smith et al. |
| 2014/0219975 A1 | 8/2014 | June et al. |
| 2015/0140665 A1 | 5/2015 | Calos et al. |
| 2016/0046700 A1 | 2/2016 | Foster et al. |
| 2016/0058857 A1 | 3/2016 | Spencer et al. |
| 2017/0166877 A1 | 6/2017 | Bayle et al. |
| 2017/0183407 A1 | 6/2017 | Cooper et al. |
| 2018/0326032 A1 | 11/2018 | Priceman et al. |
| 2020/0102366 A1 | 4/2020 | Cooper et al. |
| 2020/0399397 A1 | 12/2020 | Lee et al. |
| 2021/0024959 A1 | 1/2021 | Valamehr et al. |
| 2021/0087537 A1 | 3/2021 | Valamehr et al. |
| 2021/0139605 A1 | 5/2021 | Wang et al. |
| 2021/0163622 A1 | 6/2021 | Valamehr et al. |
| 2021/0163895 A1 | 6/2021 | Valamehr et al. |
| 2021/0308183 A1 | 10/2021 | Schrepfer et al. |
| 2021/0388389 A1 | 12/2021 | Chen et al. |
| 2022/0089750 A1 | 3/2022 | June et al. |
| 2022/0275333 A1 | 9/2022 | Valamehr et al. |
| 2022/0378831 A1 | 12/2022 | Valamehr et al. |
| 2023/0016034 A1 | 1/2023 | Valamehr et al. |
| 2024/0002531 A1 | 1/2024 | Kato et al. |
| 2024/0002532 A1 | 1/2024 | Valamehr et al. |

FOREIGN PATENT DOCUMENTS

| | | | |
|---|---|---|---|
| WO | WO 1998/053059 | A1 | 11/1998 |
| WO | WO 1998/053060 | A1 | 11/1998 |
| WO | WO 2002/016536 | A1 | 2/2002 |
| WO | WO 2003/016496 | A2 | 2/2003 |
| WO | WO 2011/159726 | A2 | 12/2011 |
| WO | WO 2017/078807 | A1 | 5/2014 |
| WO | WO 2015/134652 | A1 | 9/2015 |
| WO | WO 2016/149665 | A1 | 9/2016 |
| WO | WO 2017/066634 | A1 | 4/2017 |
| WO | WO 2017/079694 | A2 | 5/2017 |
| WO | WO 2017/127755 | A1 | 7/2017 |
| WO | WO 2019/075057 | A1 | 4/2019 |
| WO | WO 2019/112899 | A2 | 6/2019 |
| WO | WO 2019/126748 | A1 | 6/2019 |
| WO | WO 2019/191495 | A1 | 10/2019 |
| WO | WO 2020/018620 | A1 | 1/2020 |
| WO | WO 2020/188573 | A1 | 9/2020 |
| WO | WO 2020/191434 | A1 | 10/2020 |
| WO | WO 2021/071962 | A | 4/2021 |
| WO | WO 2021/077117 | A1 | 4/2021 |
| WO | WO 2021/151119 | A1 | 7/2021 |
| WO | WO 2021/235894 | A1 | 11/2021 |
| WO | WO 2022/098914 | A | 5/2022 |
| WO | WO 2022/098925 | A | 5/2022 |
| WO | WO 2022/114163 | A1 | 6/2022 |
| WO | WO 2023/196982 | A | 10/2023 |

OTHER PUBLICATIONS

Hudecek et al. The nonsignaling extracellular spacer domain of chimeric antigen receptors is decisive for in vivo antitumor activity. Cancer Immunol Res (2015) 3 (2): 125-135. https://doi.org/10.1158/2326-6066.CIR-14-0127 (Year: 2015).*

Yamada et al. Establishment of H2Mab-119, an Anti-Human Epidermal Growth Factor Receptor 2 Monoclonal Antibody, Against Pancreatic Cancer. Monoclonal Antibodies in Immunodiagnosis and Immunotherapy. Volume: 36 Issue 6: Dec. 1, 2017. 287-290.http://doi.org/10.1089/mab.2017.0050 (Year: 2017).*

Itai et al. H2Mab-77 is a Sensitive and Specific Anti-HER2 Monoclonal Antibody Against Breast Cancer. Monoclonal Antibodies in Immunodiagnosis and Immunotherapy.Aug. 2017.143-148.http://doi.org/10.1089/mab.2017.0026 (Year: 2017).*

Casneuf et al., "Effects of daratumumab on natural killer cells and impact on clinical outcomes in relapsed or refractory multiple myeloma," *Blood Adv.*, 1(23):2105-2114 (2017).

Christodoulou et al., "Engineering CAR-NK cells to secrete IL-15 sustains their anti-AML functionality but is associated with systemic toxicities," *J. Immuno Ther. Cancer*, 9(12):e003894 (2021).

Donnelly et al., "The 'cleavage' activities of foot-and-mouth disease virus 2A site-directed mutants and naturally occurring '2A-like' sequences," *J. Gen. Virol.*, 82:1027-1041 (2001).

Dragomir et al., "Key questions about the checkpoint blockade-are microRNAs an answer?," *Cancer Biol. Med.*, 15(2):103-115 (2018).

Hegde et al., "Tandem CAR T cells targeting HER2 and IL13Ra2 mitigate tumor antigen escape," *J. Clin. Invest.*, 126(8):3036-3052 (2016).

Kohli et al., "Key chemokines direct migration of immune cells in solid tumors," *Cancer Gene Ther.*, 29:10-21 (2021).

Mo et al., "Engineered off-the-shelf therapeutic T cells resist host immune rejection," *Nat. Biotechnol.*, 39(1):56-63 (2020).

Ryan et al., "Cleavage of foot-and-mouth disease virus polyprotein is mediated by residues located within a 19 amino acid sequence," *J. Gen. Virol.*, 72:2727-2732 (2001).

* cited by examiner

CHIMERIC ANTIGEN RECEPTOR FOR TUMOR TARGETING

RELATED APPLICATIONS

This application claims priority to U.S. Provisional Application Ser. No. 63/329,287, filed Apr. 8, 2022, the disclosure of which is hereby incorporated by reference in its entirety.

PARTIES TO A JOINT RESEARCH AGREEMENT

The presently claimed subject matter was made by, or on behalf of, one or more parties to a joint research agreement. The parties to the joint research agreement are Fate Therapeutics, Inc. and Ono Pharmaceutical Co., Ltd.

INCORPORATION BY REFERENCE OF SEQUENCE LISTING

The Sequence Listing titled 184143-640601_SL.xml, which was created on Apr. 1, 2023 and is 87,714 bytes in size, is hereby incorporated by reference in its entirety.

FIELD OF THE INVENTION

The present disclosure is broadly concerned with the field of off-the-shelf immunocellular products. More particularly, the present disclosure is concerned with strategies for developing solid tumor targeting chimeric antigen receptors for use in cancer treatments.

BACKGROUND OF THE INVENTION

Cancer cells emerge from normal tissues through accumulated genetic and epigenetic aberrations, and differentiate themselves from normal cells by producing proteins that differ in quantity and quality from those of normal cells. However, tumor-specific cell surface expressed membrane proteins that can be exploited as tumor antigens for an effective targeted cancer therapy have very rarely been identified, because as data have shown, these tumor cell surface expressed membrane proteins more likely than not can also be expressed on normal tissues. Therefore, targeting these molecules through chimeric antigen receptors (CARs) in solid tumors comes with an inherent risk of severe toxicities to normal tissues.

SUMMARY OF THE INVENTION

There is a need for tumor-specific and functionally improved CARs in order to develop targeted cancer treatments, and address issues such as tumor targeting precision, off-target toxicity, and off-tumor effect against solid tumors.

In one aspect, the invention provides a chimeric antigen receptor (CAR) comprising: (a) an ectodomain comprising an antigen binding domain recognizing a HER2 (human epidermal growth factor receptor 2) antigen, wherein the antigen binding domain comprises: (i) a heavy chain variable (VH) domain comprising a heavy chain complementary determining region 1 (H-CDR1) comprising SEQ ID NO: 1 (NYGMS), a heavy chain complementary determining region 2 (H-CDR2) comprising SEQ ID NO: 2 (TINNNGGGTYYPDSVKG), and a heavy chain complementary determining region 3 (H-CDR3) comprising SEQ ID NO: 3 (PGLLWDA); and (ii) a light chain variable (VL) domain comprising a light chain complementary determining region 1 (L-CDR1) comprising SEQ ID NO: 4 (KSSQSLLDSDGRTYLN), a light chain complementary determining region 2 (L-CDR2) comprising SEQ ID NO: 5 (LVSKLDS), and a light chain complementary determining region 3 (L-CDR3) comprising SEQ ID NO: 6 (WQGTHFPQT); (b) a transmembrane domain; and (c) an endodomain comprising at least one signaling domain, wherein the at least one signaling domain responds specifically to binding of the CAR to a HER2 antigen expressed on a cancer cell, thereby generating a cancer antigen specific response.

In some embodiments of the CAR, the antigen binding domain: (a) comprises a VH domain with at least 80% sequence identity to SEQ ID NO: 7 (EVQLVESGGGLVQPGGSLKLSCAASGFTFSNYGMSWVRQTPDRRLELVATINNNGGGTY YPDSVKGRFTISRDNAKNTLYLQMSSLKSEDTAMYYCTSPGLLWDAWGAGTTVTVSS); (b) comprises a VL domain with at least 80% sequence identity to SEQ ID NO: 8 (DVVMTQTPLTLSVSIGQPASISCKSSQSLLDSDGRTYLNWLLQRPGQSPKRLIYLVSKLDS GAPDRFTGSGSGTDFTLKISRVEAEDLGVYYCWQGTHFPQTFGGGTKLEIK); (c) comprises a single chain variable fragment (scFV) comprising VH-linker-VL or VL-linker-VH, wherein the linker varies in length and sequence, and optionally wherein the linker has at least 80% sequence identity to SEQ ID NO: 9 (GSTSGGGSGGGSGGGSS), SEQ ID NO: 10 (GSTSGSGKPGSGEGSTKG), SEQ ID NO: 11 (SSGGGGSGGGGSGGGGS), or SEQ ID NO: 12 (GGGGSGGGGSGGGGS); (d) comprises an scFV represented by an amino acid sequence that is of at least about 99%, about 98%, about 96%, about 95%, about 90%, about 85%, or about 80% identity to SEQ ID NO: 13 (EVQLVESGGGLVQPGGSLKLSCAASGFTFSNYGMSWVRQTPDRRLELVATINNNGGGTY YPDSVKGRFTISRDNAKNTLYLQMSSLKSEDTAMYYCTSPGLLWDAWGAGTTVTVSSGS TSGGGSGGGSGGGGSSDVVMTQTPLTLSVSIGQPASISCKSSQSLLDSDGRTYLNWLLQR PGQSPKRLIYLVSKLDSGAPDRFTGSGSGTDFTLKISRVEAEDLGVYYCWQGTHFPQTFGGGTKLEIK) or SEQ ID NO: 14 (DVVMTQTPLTLSVSIGQPASISCKSSQSLLDSDGRTYLNWLLQRPGQSPKRLIYLVSKLDSGAPDRFTGSGSGTDFTLKISRVEAEDLGVYY CWQGTHFPQTFGGGTKLEIKGSTSGGGSG GGSGGGGSSEVQLVESGGGLVQPGGSLKLSCAASGFTFSNYGMSWVRQTPDRRLELVATI NNNGGGTYYPDSVKGRFTISRDNAKNTLYLQMSSLKSEDTAMYYCTSPGLLWDAWGAG TTVTVSS), wherein each of SEQ ID NOs: 13 and 14 comprises a linker that varies in length and sequence; and/or (e) is humanized.

In some embodiments of the CAR, the at least one signaling domain comprises: (a) any one of: 2B4 (Natural killer Cell Receptor 2B4), 4-1BB (Tumor necrosis factor receptor superfamily member 9). CD16 (IgG Fc region Receptor III-A), CD2 (T-cell surface antigen CD2), CD28 (T-cell-specific surface glycoprotein CD28), CD28H (Transmembrane and immunoglobulin domain-containing protein 2), CD3ζ (T-cell surface glycoprotein CD3 zeta chain), DAP10 (Hematopoietic cell signal transducer), DAP12 (TYRO protein tyrosine kinase-binding protein), DNAM1 (CD226 antigen), FcERIγ (High affinity immunoglobulin epsilon receptor subunit gamma), IL21R (Interleukin-21 receptor), IL-2Rβ/IL-15RB (Interleukin-2 receptor subunit beta), IL-2Rγ (Cytokine receptor common subunit gamma), IL-7R (Interleukin-7 receptor subunit alpha). KIR2DS2 (Killer cell immunoglobulin-like receptor 2DS2), NKG2D (NKG2-D type II integral membrane protein), NKp30 (Natural cytotoxicity triggering receptor 3), NKp44 (Natural cytotoxicity triggering receptor 2), NKp46 (Natural cytotoxicity triggering receptor 1). CS1 (SLAM family member 7), and CD8 (T-cell surface glycoprotein CD8 alpha chain); (b) an amino acid sequence that has at least about 85%, about 90%, about 95%, about 96%, about 97%, about 98%, or about 99% identity to the cytoplasmic domain, or a portion thereof, of 2B4, 4-1BB, CD16, CD2, CD28, CD28H, CD3ζ, CD3ζ1XX, DAP10, DAP12, DNAM1, FcERIγ, IL21R, IL2Rβ (IL15Rβ), IL2Rγ, IL7R, KIR2DS2, NKG2D, NKp30, NKp44, NKp46, CS1, or CD8, represented by SEQ ID NOs: 37-59, respectively; and/or (c) an amino acid sequence that has at least about 85%, about 90%, about 95%, about 96%, about 97%, about 98%, or about 99% identity to the cytoplasmic domain, or a portion thereof, of 2B4, CD28, CD3ζ, DAP10, NKG2D, CD3ζ1XX, DNAM1, CS1, or combinations thereof. In various embodiments of the CAR, the endodomain comprises two different signaling domains, and wherein said endodomain domain comprises fused cytoplasmic domains, or portions thereof. In any one of the forms: 2B4-CD3ζ/1XX, 2B4-DNAM1, 2B4-FcERIγ, 2B4-DAP10, CD16-DNAM1, CD16-DAP10, CD16-DAP12, CD2-CD3ζ/1XX, CD2-DNAM1, CD2-FcERIγ, CD2-DAP10, CD28-DNAM1, CD28-FcERIγ, CD28-DAP10, CD28-DAP12, CD28-CD3ζ/1XX, CD28H-CD3ζ/1XX, DAP10-CD3ζ/1XX, DAP10-DAP12, DAP12-CD3ζ/1XX, DAP12-DAP10, DNAM1-CD3ζ/1XX, KIR2DS2-CD3ζ/1XX, KIR2DS2-DAP10, KIR2DS2-2B4, or NKp46-2B4.

In various embodiments of the CAR, the transmembrane domain comprises an amino acid sequence that has at least about 85%, about 90%, about 95%, about 96%, about 97%, about 98%, or about 99% identity to a transmembrane region, or a portion thereof, of: (a) CD2, CD3δ, CD3ε, CD3γ, CD3ζ, CD4, CD8, CD8a, CD8b, CD16, CD27, CD28, CD28H, CD40, CD84, CD166, 4-1BB, OX40, ICOS, ICAM-1, CTLA4, PD1, LAG3, 2B4, BTLA, DNAM1, DAP10, DAP12, FcERIγ, IL7, IL12, IL15, KIR2DL4, KIR2DS1, KIR2DS2, NKp30, NKp44, NKp46, NKG2C, NKG2D, CS1, or T cell receptor polypeptide (b) 2B4, CD2, CD16, CD28, CD28H, CD3ζ, DAP10, DAP12, DNAM1, FcERIγ, KIR2DS2, NKG2D, NKp30, NKp44, NKp46, CS1, or CD8; or (c) 2B4, CD28, CD28H, DAP10, DNAM1, KIR2DS2, and NKG2D. In some embodiments of the CAR, the transmembrane domain and its immediately linked signaling domain are from a same protein or from different proteins.

In various embodiments of the CAR, the ectodomain comprises one or more of: (a) a signal peptide; and/or (b) a spacer/hinge. In some embodiments of the CAR, the spacer/hinge comprises. (a) an IgG4 spacer, a CD28 spacers, a CD8 spacer, a CH3 spacer, a CH2/CH3 spacer, or any combination thereof; (b) a short spacer of about 10 to about 80 amino acids; a medium spacer of more than 80 to about 180 amino acids; or a long spacer of more than 180 amino acids; and/or (c) an amino acid sequence of at least about 80%, about 85%, about 90%, about 95%, about 96%, about 97%, about 98%, or about 99% identity to any of SEQ ID NOs: 81-85. In some embodiments of the CAR, the spacer/hinge comprises a medium spacer, wherein the spacer comprises an amino acid sequence of at least about 80%, about 85%, about 90%, about 95%, about 96%, about 97%, about 98%, or about 99% identity to SEQ ID NO: 84.

In various embodiments of the CAR, the CAR comprises an amino acid sequence of at least about 90%, about 95%, about 96%, about 97%, about 98%, or about 99% identity to SEQ ID NO: 88. In various embodiments of the CAR, the cancer cell is a breast cancer cell, an ovary cancer cell, an endometrium cancer cell, a lung cancer cell, an esophageal cancer cell, a salivary gland cancer cell, a bladder cancer cell, a gastric cancer cell, a colorectal cancer cell, or a head and neck cancer cell. In various embodiments of the CAR, the at least one signaling domain does not respond, or has a low level of response, to HER2 expressed on non-cancer cells. In various embodiments of the CAR, the cancer antigen specific responses comprise cytolysis and cytokine production.

In another aspect, the invention provides a polynucleotide comprising a nucleic acid sequence which encodes a CAR as described herein. In yet another aspect, the invention provides a vector comprising the polynucleotide described herein.

Various objects and advantages of the compositions and methods as provided herein will become apparent from the following description taken in conjunction with the accompanying drawings wherein are set forth, by way of illustration and example, certain embodiments of this invention.

DETAILED DESCRIPTION OF THE INVENTION

Definitions

Figure 1A:
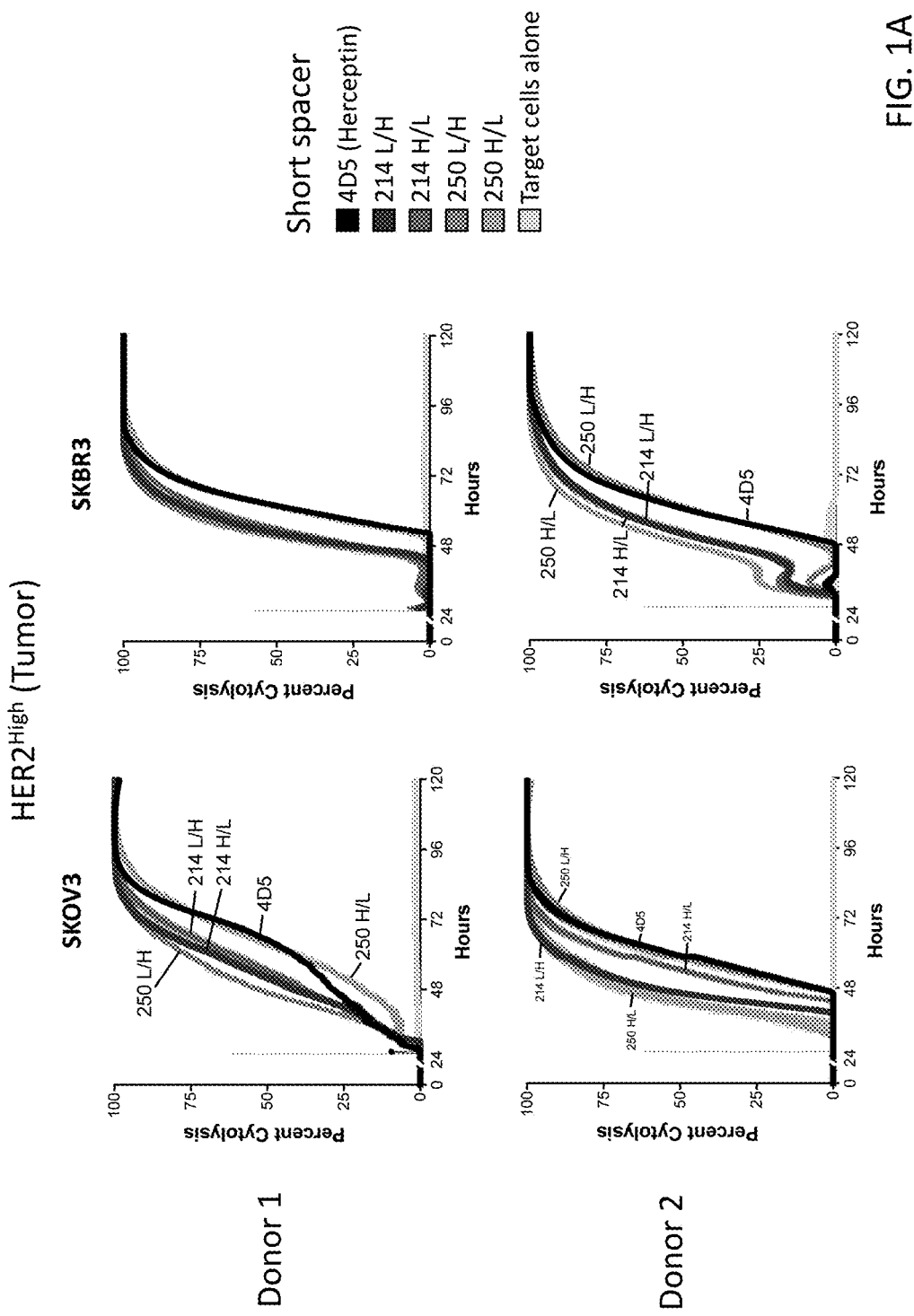
FIGS. 1A and 1B show cytolytic efficacy and specificity of 4D5-, CasMab214-, or CasMab250-based CARs with short spacers against HER2 expressing tumor cells and non-tumorigenic normal cells that express HER2.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein, the articles "a," "an," and "the" are used herein to refer to one or to more than one (i.e., to at least one) of the grammatical object of the article. By way of example, "an element" means one element or more than one element.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% compared to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

As used herein, the term "substantially" or "essentially" refers to a quantity, level, value, number, frequency, percentage, dimension, size, amount, weight or length that is about 90%, 91%, 92%, 93%, 94%, 95%, 96%, 97%, 98%, or 99% or higher compared to a reference quantity, level, value, number, frequency, percentage, dimension, size, amount, weight or length. In one embodiment, the terms "essentially the same" or "substantially the same" refer a range of quantity, level, value, number, frequency, percentage, dimension, size, amount, weight or length that is about the same as a reference quantity, level, value, number, frequency, percentage, dimension, size, amount, weight or length.

As used herein, the terms "substantially free of" and "essentially free of" are used interchangeably, and w % ben used to describe a composition, such as a cell population or culture media, refer to a composition that is free of a specified substance or its source thereof, such as, 95% free, 96% free, 97% free, 98% free, 99% free of the specified substance or its source thereof, or is undetectable as measured by conventional means. The term "free of" or "essentially free of" a certain ingredient or substance in a composition also means that no such ingredient or substance is (1) included in the composition at any concentration, or (2) included in the composition at a functionally inert, low concentration. Similar meaning can be applied to the term "absence of," where referring to the absence of a particular substance or its source thereof of a composition.

Throughout this specification, unless the context requires otherwise, the words "comprise." "comprises" and "comprising" will be understood to imply the inclusion of a stated step or element or group of steps or elements but not the exclusion of any other step or element or group of steps or elements. In particular embodiments, the terms "include," "has," "contains," and "comprise" are used synonymously.

By "consisting of" is meant including, and limited to, whatever follows the phrase "consisting of." Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

The term "ex vivo" refers generally to activities that take place outside an organism, such as experimentation or measurements done in or on living tissue in an artificial environment outside the organism, preferably with minimum alteration of the natural conditions. In particular embodiments. "ex vivo" procedures involve living cells or tissues taken from an organism and cultured in a laboratory apparatus, usually under sterile conditions, and typically for a few hours or up to about 24 hours, but including up to 48 or 72 hours or longer, depending on the circumstances. In certain embodiments, such tissues or cells can be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo.

The term "in vivo" refers generally to activities that take place inside an organism.

As used herein, the term "encoding" refers to the inherent property of specific sequences of nucleotides in a polynucleotide, such as a gene, a cDNA, or a mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

A "construct" refers to a macromolecule or complex of molecules comprising a polynucleotide to be delivered to a host cell, either in vitro or in vivo. A "vector," as used herein refers to any nucleic acid construct capable of directing the delivery or transfer of a foreign genetic material to target cells, where it can be replicated and/or expressed. The term "vector" as used herein comprises the construct to be delivered. A vector can be a linear or a circular molecule. A vector can be integrating or non-integrating. The major types of vectors include, but are not limited to, plasmids, episomal vectors, viral vectors, cosmids, and artificial chromosomes. Viral vectors include, but are not limited to, adenovirus vectors, adeno-associated virus vectors, retrovirus vectors, lentivirus vectors, Sendai virus vectors, and the like.

As used herein, the term "exogenous" is intended to mean that the referenced molecule is introduced into, or is non-native to, the host cell. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the cell. The term "endogenous" refers to a referenced molecule or activity that is present in the host cell. Similarly, the term when used in reference to expression of an encoding nucleic acid refers to expression of an encoding nucleic acid contained within the cell and not exogenously introduced.

By "integration" it is meant that one or more nucleotides of a construct is stably inserted into the cellular genome, i.e., covalently linked to the nucleic acid sequence within the cell's chromosomal DNA. By "targeted integration" it is meant that the nucleotide(s) of a construct is inserted into the cell's chromosomal or mitochondrial DNA at a pre-selected site or "integration site". The term "integration" as used herein further refers to a process involving insertion of one or more exogenous sequences or nucleotides of the construct, with or without deletion of an endogenous sequence or nucleotide at the integration site.

As used herein, a "gene of interest" or "a polynucleotide sequence of interest" is a DNA sequence that is transcribed into RNA and in some instances translated into a polypeptide in vivo when placed under the control of appropriate regulatory sequences. A gene or polynucleotide of interest can include, but is not limited to, prokaryotic sequences, cDNA from eukaryotic mRNA, genomic DNA sequences from eukaryotic (e.g., mammalian) DNA, and synthetic DNA sequences. For example, a gene of interest may encode an miRNA, an shRNA, a native polypeptide (i.e., a polypeptide found in nature) or fragment thereof: a variant polypeptide (i.e., a mutant of the native polypeptide having less than 100% sequence identity with the native polypeptide) or fragment thereof; an engineered polypeptide or peptide fragment, a therapeutic peptide or polypeptide, an imaging marker, a selectable marker, and the like.

As used herein, the term "polynucleotide" refers to a polymeric form of nucleotides of any length, either deoxyribonucleotides or ribonucleotides or analogs thereof. The sequence of a polynucleotide is composed of four nucleotide bases: adenine (A); cytosine (C); guanine (G); thymine (T); and uracil (U) for thymine when the polynucleotide is RNA. A polynucleotide can include a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. Polynucleotide also refers to both double- and single-stranded molecules.

As used herein, the terms "peptide," "polypeptide," and "protein" are used interchangeably and refer to a molecule having amino acid residues covalently linked by peptide bonds. A polypeptide must contain at least two amino acids, and no limitation is placed on the maximum number of amino acids of a polypeptide. As used herein, the terms refer to both short chains, which are also commonly referred to in the art as peptides, oligopeptides and oligomers, for example, and to longer chains, which generally are referred to in the art as polypeptides or proteins. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural polypeptides, recombinant polypeptides, synthetic polypeptides, or a combination thereof.

As used herein and throughout the application, the percent identity between two sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm recognized in the art.

As used herein, the term "subunit" as used herein refers to each separate polypeptide chain of a protein complex, where each separate polypeptide chain can form a stable folded structure by itself. Many protein molecules are composed of more than one subunit, where the amino acid sequences can either be identical for each subunit, or similar, or completely different. For example, a CD3 complex is composed of CD3α, CD3ε, CD3δ, CD3γ, and CD3ζ subunits, which form the CD3ε/CD3γ, CD3ε/CD3δ, and CD3ζ/CD3ζ dimers. Within a single subunit, contiguous portions of the polypeptide chain frequently fold into compact, local, semi-independent units that are called "domains". Many protein domains may further comprise independent "structural subunits", also called subdomains, contributing to a common function of the domain. As such, the term "subdomain" as used herein refers to a protein domain inside of a larger domain, for example, a binding domain within an ectodomain of a cell surface receptor; or a stimulatory domain or a signaling domain of an endodomain of a cell surface receptor.

"Operably-linked" or "operatively linked," interchangeable with "operably connected" or "operatively connected," refers to the association of nucleic acid sequences on a single nucleic acid fragment (or amino acids in a polypeptide with multiple domains) so that the function of one is affected by the other. For example, a promoter is operably-linked with a coding sequence or functional RNA when it is capable of affecting the expression of that coding sequence or functional RNA (i.e., the coding sequence or functional RNA is under the transcriptional control of the promoter). Coding sequences can be operably-linked to regulatory sequences in sense or antisense orientation. As a further example, a receptor-binding domain can be operatively connected to an intracellular signaling domain, such that binding of the receptor to a ligand transduces a signal responsive to said binding.

"Fusion proteins" or "chimeric proteins", as used herein, are proteins created through genetic engineering to join two or more partial or whole polynucleotide coding sequences encoding separate proteins, and the expression of these joined polynucleotides results in a single peptide or multiple polypeptides with functional properties derived from each of the original proteins or fragments thereof. Between two neighboring polypeptides of different sources in the fusion protein, a linker (or spacer) peptide can be added.

As used herein, the term "signaling molecule" refers to any molecule that modulates, participates in, inhibits, activates, reduces, or increases, cellular signal transduction. "Signal transduction" refers to the transmission of a molecular signal in the form of chemical modification by recruitment of protein complexes along a pathway that ultimately triggers a biochemical event in the cell. Signal transduction pathways are well known in the art, and include, but are not limited to, G protein coupled receptor signaling, tyrosine kinase receptor signaling, integrin signaling, toll gate signaling, ligand-gated ion channel signaling, ERK/MAPK signaling pathway, Wnt signaling pathway, cAMP-dependent pathway, and IP3/DAG signaling pathway.

As used herein, the term "specific" or "specificity" can be used to refer to the ability of a molecule, e.g., a receptor or an engager, to selectively bind to a target molecule, in contrast to non-specific or non-selective binding.

The term "ligand" refers to a substance that forms a complex with a target molecule to produce a signal by binding to a site on the target. The ligand may be a natural or artificial substance capable of specific binding to the target. The ligand may be in the form of a protein, a peptide, an antibody, an antibody complex, a conjugate, a nucleic acid, a lipid, a polysaccharide, a monosaccharide, a small molecule, a nanoparticle, an ion, a neurotransmitter, or any other molecular entity capable of specific binding to a target. The target to which the ligand binds, may be a protein, a nucleic acid, an antigen, a receptor, a protein complex, or a cell. A ligand that binds to and alters the function of the target and triggers a signaling response is called "agonistic" or "an agonist". A ligand that binds to a target and blocks or reduces a signaling response is "antagonistic" or "an antagonist."

The term "antibody" encompasses antibodies and antibody fragments that contain at least one binding site that specifically binds to a particular target of interest, wherein the target may be an antigen, or a receptor that is capable of interacting with certain antibodies. The term "antibody" includes, but is not limited to, an immunoglobulin molecule or an antigen-binding or receptor-binding portion thereof. A specific piece or portion of an antigen or receptor, or a target in general, to which an antibody binds is known as an epitope or an antigenic determinant. The term antibody also includes, but is not limited to, native antibodies and variants thereof, fragments of native antibodies and variants thereof, peptibodies and variants thereof, and antibody mimetics that mimic the structure and/or function of an antibody or a specified fragment or portion thereof, including single chain antibodies and fragments thereof. An antibody may be a murine antibody, a human antibody, a humanized antibody, a camel IgG, single variable new antigen receptor (VNAR), shark heavy-chain antibody (Ig-NAR), a chimeric antibody, a recombinant antibody, a single-domain antibody (dAb), an anti-idiotype antibody, a bi-specific-, multi-specific- or multimeric-antibody, or antibody fragment thereof. Non-limiting examples of antibody fragments include Fab, Fab', F(ab')2, F(ab')3, Fv, Fabc, pFc, Fd, single chain fragment variable (scFv), tandem scFv (scFv)2, single chain Fab (scFab), disulfide stabilized Fv (dsFv), minibody, diabody, triabody, tetrabody, single-domain antigen binding fragments (sdAb), camelid heavy-chain IgG and Nanobody® fragments, recombinant heavy-chain-only antibody (VHH), and other antibody fragments that maintain the binding specificity of the antibody.

Tumor-Specific Chimeric Antigen Receptor (CAR)

A CAR is a fusion protein generally including an ectodomain that comprises an antigen recognition region, a transmembrane domain, and an endodomain. In some embodiments, the ectodomain can further include a signal peptide or leader sequence and/or a spacer. In some embodiments, the endodomain comprises a signaling peptide that activates the effector cell expressing the CAR. In some embodiments, the endodomain comprises one or more signaling domains, wherein the signaling domain orginates from a cytoplasmic domain of a signal transducing protein specific to T and/or NK cell activation or functioning. In some embodiments, the antigen recognition domain can specifically bind an antigen. In some embodiments, the antigen recognition domain can specifically bind an antigen associated with a disease or pathogen. In some embodiments, the disease-associated antigen is a tumor antigen, wherein the tumor may be a liquid or a solid tumor.

In certain embodiments, said antigen recognition region/domain comprises a murine antibody, a human antibody, a humanized antibody, a camel Ig, a single variable new antigen receptor (VNAR), a shark heavy-chain-only antibody (Ig-NAR), a chimeric antibody, a recombinant antibody, or an antibody fragment thereof. Non-limiting examples of antibody fragments include Fab, Fab', F(ab')2, F(ab')3, Fv, single chain antigen binding fragment (scFv). (scFv)$_2$, disulfide stabilized Fv (dsFv), minibody, diabody, triabody, tetrabody, single-domain antigen binding fragments (sdAb, Nanobody), recombinant heavy-chain-only antibody (VHH), and other antibody fragments that maintain the binding specificity of the whole antibody.

Various aspects of the invention provide a CAR comprising an antigen recognition region that binds to a tumor associated antigen. In various embodiments, the CAR is specific to a tumor cell surface HER2 antigen. In some embodiments, the antigen recognition domain of the ectodomain of the HER2-CAR comprises a heavy chain variable (VH) domain comprising a heavy chain complementary determining region 1 (H-CDR1) comprising SEQ ID NO: 1 (NYGMS), a heavy chain complementary determining region 2 (H-CDR2) comprising SEQ ID NO: 2 (TINNNGGGTYYPDSVKG), and a heavy chain complementary determining region 3 (H-CDR3) comprising SEQ ID NO: 3 (PGLLWDA); and a light chain variable (VL) domain comprising alight chain complementary determining region 1 (L-CDR1) comprising SEQ ID NO: 4 (KSSQSLL-DSDGRTYLN), a light chain complementary determining region 2 (L-CDR2) comprising SEQ ID NO: 5 (LVSKLDS), and a light chain complementary determining region 3 (L-CDR3) comprising SEQ ID NO: 6 (WQGTHFPQT).

In some embodiments, the CAR comprises heavy chain CDRs followed by light chain CDRs (H/L) in an amino to carboxy direction. In some embodiments, the CAR comprises a heavy chain variable domain followed by a light chain variable domain in an amino to carboxy direction.

In some embodiments, the antigen binding domain of the CAR comprises a VH domain having a sequence identity of at least 50%, 55%, 60%, 65%, 70%, 75%, 80%, 85%, 90%, 95%, 99%, 100%, or any percentage in-between, when compared to the exemplary sequence represented by SEQ ID NO: 7. In some embodiments, the VH domain comprises an amino acid sequence of at least about 90% identity to SEQ ID NO: 7. In some embodiments, the VH domain comprises an amino acid sequence of at least about 95% identity to SEQ ID NO: 7. In some embodiments, the VH domain comprises the amino acid sequence of SEQ ID NO: 7. In some other embodiments, the antigen binding domain of the CAR comprises a VL domain having a sequence identity of at least 50%, 55%, 60%, 65%, 70%, 75%, 80%, 85%, 90%, 95%, 99%, 100%, or any percentage in-between, when compared to the exemplary sequence represented by SEQ ID NO: 8. In some embodiments, the VL domain comprises an amino acid sequence of at least about 90% identity to SEQ ID NO: 8. In some embodiments, the VL domain comprises an amino acid sequence of at least about 95% identity to SEQ ID NO: 8. In some embodiments, the VL domain comprises the amino acid sequence of SEQ ID NO: 8.

SEQ ID NO: 7
EVQLVESGGGLVQPGGSLKLSCAASGFTFSNYG

MSWVRQTPDRRLELVATINNNGGGTYYPDSVKG

RFTISRDNAKNTLYLQMSSLKSEDTAMYYCTSP

GLLWDAWGAGTTVTVSS

SEQ ID NO: 8
DVVMTQTPLTLSVSIGQPASISCKSSQSLLDSD

GRTYLNWLLQRPGQSPKRLIYLVSKLDSGAPDR

FTGSGSGTDFTLKISRVEAEDLGVYYCWQGTHF

PQTFGGGTKLEIK

In some embodiments the antigen binding domain of the CAR comprises a single chain variable fragment (scFV) having a N to C terminus orientation comprising VH-linker-VL or VL-linker-VH, wherein the linker varies in length and sequence. In some embodiments, the linker has a sequence identity of at least 50%, 55%, 60%, 65%, 70%, 75%, 80%, 85%, 90%, 95%, 99%, 100%, or any percentage in-between, when compared to the exemplary sequences represented by SEQ ID NOs: 9-12. In some embodiments, the linker comprises an amino acid sequence of at least about 90% identity to any of SEQ ID NOs: 9-12. In some embodiments, the linker comprises an amino acid sequence of at least about 95% identity to any of SEQ ID NOs: 9-12. In some embodiments, the linker comprises the amino acid sequence of any of SEQ ID NOs: 9-12.

SEQ ID NO: 9
GSTSGGGSGGGSGGGSS

SEQ ID NO: 10
GSTSGSGKPGSGEGSTKG

SEQ ID NO: 11
SSGGGGSGGGGSGGGGS

SEQ ID NO: 12
GGGGSGGGGSGGGGS

In some embodiments the antigen binding domain of the CAR comprises a single chain variable fragment (scFV) having n sequence identity of at least 50%, 55%, 60%, 65%, 70%, 75%, 80%, 85%, 90%, 95%, 99%, 100%, or any percentage in-between, when compared to the exemplary sequences represented by SEQ ID NO: 13 or SEQ ID NO: 14, wherein each of SEQ ID NOs: 13 and 14 comprise a linker that can vary in length and/or sequence. In some embodiments, the scFV comprises an amino acid sequence of at least 90% identity to SEQ ID NO: 13 or 14. In some embodiments, the scFV comprises an amino acid sequence of at least 95% identity to SEQ ID NO: 13 or 14. In some embodiments, the scFV comprises the amino acid sequence of SEQ ID NO: 13. In some embodiments, the scFV comprises the amino acid sequence of SEQ ID NO: 14.

SEQ ID NO: 13
EVQLVESGGGLVQPGGSLKLSCAASGFTFSNYGMSWVRQT

PDRRLELVATINNNGGGTYYPDSVKGRFTISRDNAKNTLY

LQMSSLKSEDTAMYYCTSPGLLWDAWGAGTTVTVSSGSTS

GGGSGGGSGGGGSSDVVMTQTPLTLSVSIGQPASISCKSS

QSLLDSDGRTYLNWLLQRPGQSPKRLIYLVSKLDSGAPDR

FTGSGSGTDFTLKISRVEAEDLGVYYCWQGTHFPQTFGGG

TKLEIK

SEQ ID NO: 14
DVVMTQTPLTLSVSIGQPASISCKSSQSLLDSDGRTYLNW

LLQRPGQSPKRLIYLVSKLDSGAPDRFTGSGSGTDFTLKI

SRVEAEDLGVYYCWQGTHFPQTFGGGTKLEIKGSTSGGGS

GGGSGGGGSSEVQLVESGGGLVQPGGSLKLSCAASGFTFS

NYGMSWVRQTPDRRLELVATINNNGGGTYYPDSVKGRFTI

SRDNAKNTLYLQMSSLKSEDTAMYYCTSPGLLWDAWGAGT

TVTVSS

In various embodiments, CARs described herein include at least an ectodomain, a transmembrane domain, and an endodomain. In some embodiments, the endodomain of a CAR comprises at least one signaling domain that is activated upon antigen binding. In some embodiments of the CAR endodomain, one or more co-stimulation domains (oftentimes referred to as "additional signaling domain(s)") is further included for optimized functionality. Exemplary signal transducing proteins suitable for a CAR design include, but are not limited to, 2B4, 4-1BB (CD137, or "41BB" in illustrative fusion constructs throughout the application), CD16, CD2, CD28, CD28H, CD3ζ/1XX (i.e., CD3ζ or CD3ζ1XX), DAP10, DAP12, DNAM1, FcERIγ, IL21R, IL-2Rβ (IL-15Rβ), IL-2Rγ, IL-7R, KIR2DS2, NKG2D, NKp30, NKp44, NKp46, CS1 and CD8. The description of exemplary signal transducing proteins, including transmembrane and cytoplasmic sequences of the proteins are provided below, and further in Table 1A.

TABLE 1A

| | Protein name | UniProtKB Accession No. | Transmembrane Sequence | Cytoplasmic Sequence |
|---|---|---|---|---|
| 2B4 | Natural killer cell receptor 2B4 | Q9BZW8 | FLVIIVILSA LFLGTL ACFCV (SEQ ID NO: 15) | WRRKRKEKQSETSPKEFLTIYEDVK DLKTRRNHEQEQTFPGGGSTIYSMI QSQSSAPTSQEPAYTLYSLIQPSRKS GSRKRNHSPSFNSTIYEVIGKSQPKA QNPARLSRKELENFDVYS (SEQ ID NO: 37) |

TABLE 1A-continued

| Protein name | | UniProtKB Accession No. | Transmembrane Sequence | Cytoplasmic Sequence |
|---|---|---|---|---|
| 4-1BB | Tumor necrosis factor receptor superfamily member 9 | Q07011 | IISFFLALTSTALL FLLFFLTLRFSVV (SEQ ID NO: 16) | KRGRKKLLYIFKQPFMRPVQTTQEE DGCSCRFPEEEEGGCEL (SEQ ID NO: 38) |
| CD16 | IgG Fc region Receptor III-A | P08637 | VSFCLVMVLLFAVD TGLYFSVKTNIRSST RD (SEQ ID NO: 17) | WKDHKFKWRKDPQDK (SEQ ID NO: 39) |
| CD2 | T-cell surface antigen CD2 | P06729 | IYLIIGICGGGSLLM VFVALLVFYITKRK KQRSRRNDEELETR AHRVATEERGRKPH QIPASTPONPATSQH PPPPPGHRSQAPSHR PPPPGHRVQ (SEQ ID NO: 18) | HQPQKRPPAPSGTQVHQQKGPPLPR PRVQPKPPHGAAENSLSPSSN (SEQ ID NO: 40) |
| CD28 | T-cell-specific surface glycoprotein CD28 | P10747 | FWVLVVVGGVLAC YSLLVTVAFIIFWV (SEQ ID NO: 19) | RSKRSRLLHSDYMNMTPRRPGPTR KHYQPYAPPRDFAAYRS (SEQ ID NO: 41) |
| CD28H | Transmembrane and immunoglobulin domain-containing protein 2 | Q96BF3 | FLFVLLGVGSMGVA AIVWGAW (SEQ ID NO: 20) | FWGRRSCQQRDSGNSPGNAFYSNV LYRPRGAPKKSEDCSGEGKDQRGQ SIYSTSFPQPAPRQPHLASRPCPS PRPCPSPRPGHPVSMVRVSPRPSP TQQPRPKGFPKVGEE (SEQ ID NO: 42) |
| CD3ζ/ 1XX | T-cell surface glycoprotein CD3 zeta chain | P20963 | LCYLLDGILFIYGVI LTALFL (SEQ ID NO: 21) | RVKFSRSADAPAYQQGQNQLYNEL NLGRREEYDVLDKRRGRDPEMGG KPQRRKNPQEGLYNELQKDKMAE AYSEIGMKGERRRGKGHDGLYQGL STATKDTYDALHMQALPPR (SEQ ID NO: 43; CD3ζ) Or RVKFSRSADAPAYQQGQNQLYNEL NLGRREEYDVLDKRRGRDPEMGG KPRRKNPQEGLFNELQKDKMAEAF SEIGMKGERRRGKGHDGLFQGLST ATKDTFDALHMQALPPR (SEQ ID NO: 44; containing 2 mutations in ITAM1; CD3ζ(1XX) |
| DAP10 | Hematopoietic cell signal transducer | Q9UBK.5 | LLAGLVAADAVASL LIVGAVF (SEQ ID NO: 22) | LCARPRRSPAQEDGKVYINMPGRG (SEQ ID NO: 45) |
| DAP12 | TYRO protein tyrosine kinase-binding protein | O43914 | GVLAGIVMGDLVLT VLIALAV (SEQ ID NO: 23) | YFLGRLVPRGRGAAEAATRKQRITE TESPYQELQGQRSDVYSDLNTQRPY YK (SEQ ID NO: 46) |
| DNAMI | CD226 antigen | Q15762 | GGTVLLLLFVISITTI IVIFL (SEQ ID NO: 24) | NRRRRRERRDLFTESWDTQKAPNN YRSPISTSQPTNQSMDDTREDIYVN YPTFSRRPKTRV (SEQ ID NO: 47) |
| FcERIγ | High affinity immunoglobulin epsilon receptor subunit gamma | P30273 | CYILDAILFLYGIVL TLLYC (SEQ ID NO: 25) | RLKIQVRKAAITSYEKSDGVYTGLS TRNQETYETLKHEKPPQ (SEQ ID NO: 48) |
| IL-21R | Interleukin-21 receptor | Q9HBE5 | GWNPHLLLLLLLVI VFIPAFW (SEQ ID NO: 26) | SLKTHPLWRLWKKIWAVPSPERFF MPLYKGCSGDFKKWVGAPFTGSSL ELGPWSPEVPSTLEVYSCHPPRSPA |

TABLE 1A-continued

| Protein name | | UniProtKB Accession No. | Transmembrane Sequence | Cytoplasmic Sequence |
|---|---|---|---|---|
| | | | | KRLQLTELQEPAELVESDGVPKPSF WPTAQNSGGSAYSEERDRPYGLVSI DTVTVLDAEGPCTWPCSCEDDGYP ALDLDAGLEPSPGLEDPLLDAGTTV LSCGCVSAGSPGLGGPLGSLLDRLK PPLADGEDWAGGLPWGGRSPGGVS ESEAGSPLAGLDMDTFDSGFVGSDC SSPVECDFTSPGDEGPPRSYLRQWV VIPPPLSSPGPQAS (SEQ ID NO: 49) |
| IL-2Rβ (IL-15Rβ) | Interleukin-2 receptor subunit beta | P14784 | IPWLGHLLVGLSGA FGFIILVYLLI (SEQ ID NO: 27) | NCRNTGPWLKKVLKCNTPDPSKFF SQLSSEHGGDVQKWLSSPFPSSSFSP GGLAPEISPLEVLERDKVTQLLLQQ DKVPEPASLSSNHSLTSCFTNQGYF FFHLPDALEIEACQVYFTYDPYSEE DPDEGVAGAPTGSSPQPLQPLSGED DAYCTFPSRDDLLLFSPSLLGGPSPP STAPGGSGAGEERMPPSLQERVPRD WDPQPLGPPTPGVPDLVDFQPPPEL VLREAGEEVPDAGPREGVSFPWSRP PGQGEFRALNARLPLNTDAYLSLQE LQGQDPTHLV (SEQ ID NO: 50) |
| IL-2Rγ | Cytokine receptor common subunit gamma | P31785 | VVISVGSMGLIISLL CVYFWL (SEQ ID NO: 28) | ERTMPRIPTLKNLEDLVTEYHGNES AWSGVSKGLAESLQPDYSERLCLV SEIPPKGGALGEGPGASPCNQHSPY WAPPCYTLKPET (SEQ ID NO: 51) |
| IL-7R | Interleukin-7 receptor subunit alpha | P16871 | PILLTISILSFFSVA LLVILACVLW (SEQ ID NO: 29) | KKRIKPIVWPSLPDHKKTLEHLCKK PRKNLNVSFNPESFLDCQIHRVDDI QARDEVEGFLQDTFPQQLEESEKQR LGGDVQSPNCPSEDVVITPESFGRD SSLTCLAGNVSACDAPILSSSRSLDC RESGKNGPHVYQDLLLSLGTTNSTL PPPFSLQSGILTLNPVAQGQPILTS LGSNQEEAYVTMSSFYQNQ (SEQ ID NO: 52) |
| KIR2DS2 | Killer cell immunoglobulin-like receptor 2DS2 | P43631 | VLIGTSVVKIPFTI LLFFLL (SEQ ID NO: 30) | HRWCSNKKNAAVMDQEPAGNRTV NSEDSDEQDHQEVSYA (SEQ ID NO: 53) |
| NKG2D | NKG2-D type II integral membrane protein | P26718 | PFFFCCFIAVAMGIR FIIMVA (SEQ ID NO: 31) | IWSAVFLNSLFNQEVQIPLTESYCG PCPKNWICYKNNCYQFFDESKNWYE SQASCMSQNASLLKVYSKEDQDLLK LVKSYHWMGLVHIPTNGSWQWEDG SILSPNLLTIIEMQKGDCALYASS FKGYIENCSTPNTYICMQRTV (SEQ ID NO: 54) |
| NKp30 | Natural cytotoxicity triggering receptor 3 | O14931 | AGTVLLLRAGFYAV SFLSVAV (SEQ ID NO: 32) | GSTVYYQGKCLTWKGPRRQLPAVV PAPLPPPCGSSAHLLPPVPGG (SEQ ID NO: 55) |
| NKp44 | Natural cytotoxicity triggering receptor 2 | O95944 | LVPVFCGLLVAKSL VLSALLV (SEQ ID NO: 33) | WWGDIWWKTMMELRSLDTQKAT CHLQQVTDLPWTSVSSPVEREILYH TVARTKISDDDDEHTL (SEQ ID NO: 56) |
| NKp46 | Natural cytotoxicity triggering receptor 1 | O76036 | GLAFLVLVALVWFL VEDWLS (SEQ ID NO: 34) | RKRTRERASRASTWEGRRRLNTQT L (SEQ ID NO: 57) |
| CS1 | SLAM family member 7 | Q9NQ25 | VLLCLLLVPLLLSLF VLGLFL (SEQ ID NO: 35) | WFLKREREQEEYIEEKKRVDICRETP NICPHSGENTEYDTIPHTNRTILKE DPANTVYSTVEIPKKMENPHSLLTM DPTPRLFAYENVI (SEQ ID NO: 58) |

TABLE 1A-continued

| Protein name | | UniProtKB Accession No. | Transmembrane Sequence | Cytoplasmic Sequence |
|---|---|---|---|---|
| CD8 | T-cell Surface Glycoprotein CD8 alpha chain | P01732 | IYIWAPLAGTC (SEQ ID NO: 36) | GVLLLSLVITLYCNHRNRRRVCKCP RPVVKSGDKPSLSARYV (SEQ ID NO: 59) |

In some embodiments of the CAR as provided, the endodomain of the CAR comprises at least a first signaling domain having an amino acid sequence that has at least about 85%, about 90%, about 95%, about 96%, about 97%, about 98%, or about 99% identity to the cytoplasmic domain, or a portion thereof, of 2B4, 4-1BB, CD16, CD2, CD28, CD28H, CD3ζ, CD3ζ1XX, DAP10, DAP12, DNAM1, FcERIγ IL21R, IL-2Rβ (IL-15Rβ), IL-2Rγ, IL-7R, KIR2DS2, NKG2D, NKp30, NKp44, NKp46, CS1, or CD8, represented by SEQ ID NOs: 37-59, respectively. In some embodiments, the first signaling domain comprises an amino acid sequence of at least 90% identity to any of SEQ ID NOs: 37-59. In some embodiments, the first signaling domain comprises an amino acid sequence of at least 95% identity to any of SEQ ID NOs: 37-59. In some embodiments, the first signaling domain comprises the amino acid sequence of any of SEQ ID NOs: 37-59. In some embodiments, the signaling domain of a CAR disclosed herein comprises only a portion of the cytoplasmic domain of 2B4, 4-1BB, CD16, CD2, CD28, CD28H, CD3ζ, CD3ζ1XX, DAP10, DAP12, DNAM1, FcERIγ IL21R, IL-2Rβ (IL-15Rβ), IL-2Rγ, IL-7R, KIR2DS2, NKG2D, NKp30, NKp44, NKp46, CS1, or CD8. In some embodiments, the portion of the cytoplasmic domain selected for the CAR signaling domain comprises an amino acid sequence that has at least about 85%, about 90%, about 95%, about 96%, about 97%, about 98%, or about 99% identity to an ITAM (immunoreceptor tyrosine-based activation motif), a YxxM motif, a TxYxxV/I motif, FcRγ, hemi-ITAM, and/or an ITT-like motif.

In some embodiments of the CAR as provided, the endodomain of the CAR comprising a first signaling domain further comprises a second signaling domain comprising an amino acid sequence that has at least about 85%, about 90%, about 95%, about 96%, about 97%, about 98%, or about 99% identity to the cytoplasmic domain, or a portion thereof, of 2B4, 4-1BB, CD16, CD2, CD28, CD28H, CD3ζ, CD3ζ1XX, DAP10, DAP12, DNAM1, FcERIγ IL21R, IL-2Rβ (IL-15Rβ), IL-2Rγ, IL-7R, KIR2DS2, NKG2D, NKp30, NKp44, NKp46, CS1 or CD8, represented by SEQ ID NOs: 37-59, respectively, wherein the second signaling domain is different from the first signaling domain. In some embodiments, the second signaling domain comprises an amino acid sequence of at least 90% identity to any of SEQ ID NOs: 37-59. In some embodiments, the second signaling domain comprises an amino acid sequence of at least 95% identity to any of SEQ ID NOs: 37-59. In some embodiments, the second signaling domain comprises the amino acid sequence of any of SEQ ID NOs: 37-59.

In some embodiments of the CAR as provided, the endodomain of the CAR comprising a first and a second signaling domain further comprises a third signaling domain comprising an amino acid sequence that has at least about 85%, about 90%, about 95%, about 96%, about 97%, about 98%, or about 99% identity to the cytoplasmic domain, or a portion thereof, of 2B4, 4-1BB, CD16, CD2, CD28, CD28H, CD3ζ, CD3ζ1XX, DAP10, DAP12, DNAM1, FcERIγ, IL21R, IL-2Rβ (IL-15Rβ), IL-2Rγ, IL-7R, KIR2DS2, NKG2D, NKp30, NKp44, NKp46, CS1, or CD8, represented by SEQ ID NOs: 37-59, respectively, wherein the third signaling domain is different from the first and the second signaling domains. In some embodiments, the third signaling domain comprises an amino acid sequence of at least 90% identity to any of SEQ ID NOs: 37-59. In some embodiments, the third signaling domain comprises an amino acid sequence of at least 95% identity to any of SEQ ID NOs: 37-59. In some embodiments, the third signaling domain comprises the amino acid sequence of any of SEQ ID NOs: 37-59. In some embodiments, signal transducing proteins suitable for designing a signaling domain of a CAR endodomain further comprise CD27, OX40, ICOS, PD-1, LAG-3, BTLA, or CTLA-4.

In some exemplary embodiments of a CAR having an endodomain comprised of only one signaling domain, said endodomain comprises an amino acid sequence that has at least about 85%, about 90%, about 95%, about 96%, about 97%, about 98%, or about 99% identity to the cytoplasmic domain or a portion thereof, of a protein including, but not limited to, DNAM1, CD28H, KIR2DS2, DAP12 or DAP10.

In some exemplary embodiments of a CAR having an endodomain comprised of two different signaling domains, said endodomain comprises fused cytoplasmic domains, or portions thereof, in a form including, but not limited to, 2B4-CD3ζ/1XX (i.e., 2B4-CD3ζ or 2B4-CD3ζ1XX; same below), 2B4-DNAM1, 2B4-FcERIγ, 2B4-DAP10, CD16-DNAM1, CD16-DAP10, CD16-DAP12, CD2-CD3ζ/1XX, CD2-DNAM1, CD2-FcERIγ, CD2-DAP10, CD28-DNAM1, CD28-FcERIγ, CD28-DAP10, CD28-DAP12, CD28-CD3ζ/1XX, CD28H-CD3ζ/1XX, DAP10-CD3ζ/1XX, DAP10-DAP12, DAP12-CD3ζ/1XX, DAP12-DAP10, DNAM1-CD3ζ/1XX, KIR2DS2-CD3ζ/1XX, KIR2DS2-DAP10, KIR2DS2-2B4, or NKp46-2B4.

In some exemplary embodiments of a CAR having an endodomain comprised of three different signaling domains, said endodomain comprises fused cytoplasmic domains, or portions thereof, in a form including, but not limited to, 2B4-DAP10-CD3ζ/1XX, 2B4-IL21R-DAP10, 2B4-IL2RB-DAP10, 2B4-IL2RB-CD3ζ/1XX, 2B4-41BB-DAP10, CD16-2B4-DAP10, or KIR2DS2-2B4-CD3ζ/1XX.

In some embodiments, the transmembrane domain of a CAR comprises an amino acid sequence that has at least about 85%, about 90%, about 95%, about 96%, about 97%, about 98%, or about 99% identity to a full length or a portion of the transmembrane region of CD2, CD3δ, CD3ε, CD3γ, CD3ζ, CD4, CD8, CD8a, CD8b, CD16, CD27, CD28, CD28H, CD40, CD84, CD166, 4-1BB, OX40, ICOS, ICAM-1, CTLA4, PD1, LAG3, 2B4, BTLA, DNAM1, DAP10, DAP12, FcERIγ, IL7, IL12, IL15, KIR2DL4, KIR2DS1, KIR2DS2, NKp30, NKp44, NKp46, NKG2C, NKG2D, CS1, or T cell receptor polypeptide. In some other embodiments, the transmembrane domain of a CAR comprises an amino acid sequence that has at least about 85%, about 90%, about 95%, about 96%, about 97%, about 98%, or about 99% identity to a full length or a portion of the transmembrane region of (a) 2B4, CD16, CD2, CD28, CD28H, CD3ζ, DAP10, DAP12, DNAM1, FcERIγ, KIR2DS2, NKG2D, NKp30, NKp44, NKp46, CS1, or CD8, represented by SEQ ID NOs: 15, 17-25, 30-36, respectively; or of (b) 2B4, CD28. CD28H, DAP10, DNAM1, KIR2DS2, and NKG2D. In some embodiments, the transmembrane domain comprises an amino acid sequence of at least about 90% identity to any of SEQ ID NOs: 15, 17-25, 30-36. In some embodiments, the transmembrane domain comprises an amino acid sequence of at least about 95% identity to any of SEQ ID NOs: 15, 17-25, 30-36. In some embodiments, the transmembrane domain comprises the amino acid sequence of any of SEQ ID NOs: 15, 17-25, 30-36. In some embodiments of the CAR, the transmembrane domain and its immediately linked signaling domain are from the same protein. In some other embodiments of the CAR, the transmembrane domain and the signaling domain that is immediately linked are from different proteins.

Table 1B of the application provides non-limiting examples of CAR constructs comprising a transmembrane domain (TM) and an endodomain (labelled as: TM-(endodomain)). In general, the illustrated CAR constructs each comprise a transmembrane domain, and an endodomain comprising one or more signaling domains derived from the cytoplasmic region of one or more signal transducing proteins. In general, a transmembrane domain is a three-dimensional protein structure which is thermodynamically stable in a membrane such as the phospholipid bilayer of a biological membrane (e.g., a membrane of a cell or cell vesicle). Thus, in some embodiments, the transmembrane domain of a CAR of the present invention comprises a single alpha helix, a stable complex of several transmembrane alpha helices, a transmembrane beta barrel, a beta-helix of gramicidin A. or any combination thereof. In various embodiments, the transmembrane domain of the CAR comprises all or a portion of a "transmembrane protein" or "membrane protein" that is within the membrane. As used herein, a "transmembrane protein" or "membrane protein" is a protein located at and/or within a membrane. Examples of transmembrane proteins that are suitable for providing a transmembrane domain comprised in a CAR of embodiments of the invention include, but are not limited to, a receptor, a ligand, an immunoglobulin, a glycophorin, or any combination thereof. In some embodiments, the transmembrane domain comprised in the CAR comprises all or a portion of a transmembrane domain of 2B4, 4-1BB, BTLA, CD2, CD3δ, CD3ε, CD3γ, CD3ζ, CD4, CD8, CD8a, CD8b, CD16, CD27, CD28, CD28H, CD40, CD84, CD166, CS1, CTLA-4, DNAM1, DAP10, DAP12, FcERIγ, ICOS, ICAM-1, IL7, IL12, IL15. KIR2DL4, KIR2DS1, KIR2DS2, LAG3, PD1. NKp30, NKp44, NKp46, NKG2C, NKG2D, OX40, T cell receptor polypeptide (such as TCRα and/or TCRPβ), a nicotinic acetylcholine receptor, a GABA receptor, or any combination thereof.

In some embodiments, one or more signaling domains comprised in the CAR endodomain are derived from the same or a different protein from which the TM is derived. As shown in Table 1B, the portion representing the transmembrane domain of the CAR is underlined, the domains comprised in the endodomain appear in parenthesis, "( )", with each of the TM and signaling domains designated by the name of the signal transducing protein from which the domain sequence is derived. In embodiments, the amino acid sequence of each TM or signaling domains may be of about 85%, about 90%, about 95%, about 96%, about 97%, about 98%, or about 99% identity to a full length or a portion of the corresponding transmembrane or cytoplasmic regions of the designated signal transducing protein. Exemplary CAR constructs comprising a transmembrane domain and an endodomain as provided herein include, but are not limited to: NKG2D-(2B4-IL2RB-CD3ζ), CD8-(41BB-CD3ζ1XX), CD28-(CD28-2B4-CD3ζ), CD28-(CD28-CD3 ζ 1XX), CD28H-(CD28H-CD3ζ), DNAM1-(DNAM1-CD3ζ), DAP10-(DAP10-CD3ζ), KIR2DS2-(KIR2DS2-CD3ζ). KIR2DS2-(KIR2DS2-DAP10), KIR2DS2-(KIR2DS2-2B4), CD16-(CD16-2B4-DAP10), CD16-(CD16-DNAM1), NKp46-(NKp46-2B4), NKp46-(NKp46-2B4-CD3ζ), NKp6-(NKp46-CD2-DAP10), CD2-(CD2-CD3ζ), 2B4-(2B4-CD3ζ), 2B4-(2B4-FcERIγ), and CS1-(CS1-CD3ζ). In some embodiments, each of the above exemplary CAR constructs comprising a transmembrane domain and an endodomain comprises an amino acid sequence of at least about 85%, about 90%, about 95%, about 96%, about 97%, about 98%, about 99%, or 100% identity to a sequence represented by each of SEQ ID NOs: 60-78 in Table 1B. In some embodiments, the CAR comprises an amino acid sequence of at least about 90% identity to any of SEQ ID NOs: 60-78. In some embodiments, the CAR comprises an amino acid sequence of at least about 95% identity to any of SEQ ID NOs: 60-78. In some embodiments, the CAR comprises the amino acid sequence of any of SEQ ID NOs: 60-78. The illustrative sequence for each construct provided in Table 1B has text formatted to match the formatting of the corresponding region in the illustration at left of the sequence (i.e., underlined, normal, or bolded text). For most of the illustrative constructs of Table 1B, the TM is the first sequence region; however, constructs may include an extracellular domain preceeding the TM (see, e.g., Construct 7 in Table 1B), and may be from the same or a different protein as the TM. In some embodiments, two or more signaling domains comprised in the CAR endodomain may be separated by one or more additional sequences, such as a spacer or a linker.

TABLE 1B

| Construct | Sequence Domains TM-(endodomain) | Illustrative Sequence | SEQ ID NO |
|---|---|---|---|
| | NKG2D-(2B4-IL2Rβ-CD3ζ) | SNLFVASWIAVMIIFRIGMAVAIFCCFFFPSWRRKRKEK QSETSPKEFLTIYEDVKDLKTRRNHEQEQTFPGGGSTI YSMIQSQSSAPTSQEPAYTLYSLIQPSRKSGSRKRNHSP SFNSTIYEVIGKSQPKAQNPARLSRKELENFDVYSNCR NTGPWLKKVLKCNTPDPSKFFSQLSSEHGGDVQKWLSSP FPSSSFSPGGLAPEISPLEVLERDKVTQLLLQQDKVPEPAS LSSNHSLTSCFTNQGYFFFHLPDALEIEACQVYFTYDPYS EEDPDEGVAGAPTGSSPQPLQPLSGEDDAYCTFPSRDDLL | 60 |

TABLE 1B-continued

| Construct | Sequence Domains TM-(endodomain) | Illustrative Sequence | SEQ ID NO |
|---|---|---|---|
| | | LFSPSLLGGPSPPSTAPGGSGAGEERMPPSLQERVPRDWD PQPLGPPTPGVPDLVDFQPPPELVLREAGEEVPDAGPREG VSFPWSRPPGQGEFRALNARLPLNTDAYLSLQELQGQDP THLVRVKFSRSADAPAYQQGQNQLYNELNLGRREEY DVLDKRRGRDPEMGGKPRRKNPQEGLYNELQKDKM AEAYSEIGMKGERRRGKGHDGLYQGLSTATKDTYDA LHMQALPPR | |
| 2 | CD8-(41BB-<br>CD3ζ1XX) | <u>IYIWAPLAGTCGVLLLSLVITLYC</u>KRGRKKLLYIFKQPF MRPVQTTQEEDGCSCRFPEEEEGGCELRVKFSRSADA PAYQQGQNQLYNELNLGRREEYDVLDKRRGRDPEMGG KPRRKNPQEGLFNELQKDKMAEAFSEIGMKGERRRGKG HDGLFQGLSTATKDTFDALHMQALPPR | 61 |
| 3 | CD28-(CD28-<br>2B4-CD3ζ) | <u>FWVLVVVGGVLACYSLLVTVAFIIFWV</u>RSKRSRLLHSDY MNMTPRRPGPTRKHYQPYAPPRDFAAYRSWRRKRKEK QSETSPKEFLTIVEDVKDLKTRRNHEQEQTFPGGGSTI YSMIQSQSSAPTSQEPAYTLYSLIQPSRKSGSRKRNHSP SFNSTIVEVIGKSQPKAQNPARLSRKELENFDVYSRVK FSRSADAPAYQQGQNQLYNELNLGRREEYDVLDKRRGR DPEMGGKPRRKNPQEGLYNELQKDKMAEAYSEIGMKGE RRRGKGHDGLYQGLSTATKDTYDALHMQALPPR | 62 |
| 4 | CD28-(CD28-<br>CD3ζ1XX) | <u>FWVLVVVGGVLACYSLLVTVAFIIFWV</u>RSKRSRLLHSDY MNMIPRRPGPTRKHYQPYAPPRDFAAYRSRVKFSRSAD APAYQQGQNQLYNELNLGRREEYDVLDKRRGRDPE MGGKPRRKNPQEGLFNELQKDKMAEAFSEIGMKGE RRRGKGHDGLFQGLSTATKDTFDALHMQALPPR | 63 |
| 5 | CD28H-<br>(CD28H-CD3ζ) | <u>FLFVLLGVGSMGVAAIVWGAWFWG</u>RRSCQQRDSGNSP GNAFYSNVLYRPRGAPKKSEDCSGEGKDQRGQSIYSTSF PQPAPRQPHLASRPCPSPRPCPSPRPGHPVSMVRVSPR PSPTQQPRPKGFPKVGEERVKFSRSADAPAYQQGQNQL YNELNLGRREEYDVLDKRRGRDPEMGGKPRRKNPQEGL YNELQKDKMAEAYSEIGMKGERRRGKGHDGLYQGL STATKDTYDALHMQALPPR | 64 |
| 6 | DNAM1-<br>(DNAM1-CD3ζ) | <u>GGTVLLLLFVISITTIIVIFL</u>NRRRRERRDLFTESWDTQK APNNYRSPISTSQPTNQSMDDTREDIYVNYPTFSRRPKTR VRVKFSRSADAPAYQQGQNQLYNELNLGRREEYDVL DKRRGRDPEMGGKPRRKNPQEGLYNELQKDKMAEA YSEIGMKGERRRGKGHDGLYQGLSTATKDTYDALH MQALPPR | 65 |
| 7 | DAP10-(DAP10-<br>CD3ζ) | TTPGERSSLPAFYPGTSGSCSGCGSLSLPLLAGLVAADAV <u>ASLLIVGAVFLC</u>ARPRRSPAQEDGKVYINMPGRGRVKFS RSADAPAYQQGQNQLYNELNLGRREEYDVLDKRRGR DPEMGGKPRRKNPQEGLYNELQKDKMAEAYSEIGM KGERRRGKGHDGLYQGLSTATKDTYDALHMQALPP R | 66 |
| 8 | KIR2DS2-<br>(KIR2DS2-<br>CD3ζ) | <u>VLIGTSVVKIPFTILLFFLL</u>HRWCSNKKNAAVMDQEPAG NRTVNSEDSDEQDHEVSYARVKFSRSADAPAYQQGQ NQLYNELNLGRREEYDVLDKRRGRDPEMGGKPRRK NPQEGLYNELQKDKMAEAYSEIGMKGERRRGKGHD GLYQGLSTATKDTYDALHMQALPPR | 67 |
| 9 | KIR2DS2-<br>(KIR2DS2-<br>DAP10) | <u>VLIGTSVVKIPFFILLFELL</u>HRWCSNKKNAAVMDQEPAG NRTVNSEDSDEQDHQEVSYALCARPRRSPAQEDGKVYI NMPGRG | 68 |
| 10 | KIR2DS2-<br>(KIR2DS2-<br>2B4) | <u>VLIGTSVVKIPFTILLFFLL</u>HRWCSNKKNAAVMDQEPAG NRTVNSEDSDEQDHQEVSYAWRRKRKEKQSETSPKEF LTIVEDVKDLKTRRNHEQEQTFPGGGSTIYSMIQSQSS APTSQEPAYTLYSLIQPSRKSGSRKRNHSPSFNSTIYEV IGKSQPKAQNPARLSRKELENFDVYS | 69 |
| 11 | CD16-(CD16-<br>2B4-DAP10) | <u>VSFCLVMVLLFAVDIGLYFSV</u>KTNIRSSTRDWKDHKFK WRKDPQDKWRRKRKEKQSETSPKEFLTIYEDVKDLK TRRNHEQEQTFPGGGSTIYSMIQSQSSAPTSQEPAYTL YSLIQPSRKSGSRKRNHSPSFNSTIYEVIGKSQPKAQNP ARLSRKELENFDVYSLCARPRRSPAQEDGKVYINMPGR G | 70 |

TABLE 1B-continued

| Construct | Sequence Domains TM-(endodomain) | Illustrative Sequence | SEQ ID NO |
|---|---|---|---|
| 12 | CD16-(CD16-DNAM1) | VSFCLVMVLLFAVDTGLYFSVKTNIRSSTRDWKDHKFK WRKDPQDKNRRRRRERRDLFTESWDTQKAPNNYRSPI STSQPTNQSMDDTREDIYVNYPTFSRRPKTRV | 71 |
| 13 | NKp46-(NKp46-2B4) | MGLAFLVLVALVWFLVEDWLSRKRTRERASRASTWEGR RRLNTQTLWRRKRKEKQSETSPKEFLTIYEDVKDLKT RRNHEQEQTFPGGGSTIYSMIQSQSSAPTSQEPAYTLY SLIQPSRKSGSRKRNHSPSFNSTIYEVIGKSQPKAQNPA RLSRKELENFDVYS | 72 |
| 14 | NKp46-(NKp46-2B4-CD3ζ) | MGLAFLVLVALVWELVEDWLSRKRTRERASRASTWEGR RRLNTQTLWRRKRKEKQSETSPKEFLTIYEDVKDLKT RRNHEQEQTFPGGGSTIYSMIQSQSSAPTSQEPAYTLY SLIQPSRKSGSRKRNHSPSFNSTIYEVIGKSQPKAQNPA RLSRKELENFDVYSRVKFSRSADAPAYQQGQNQLYNEL NLGRREEYDVLDKRRGRDPEMGGKPRRKNPQEGLYNEL QKDKMAEAYSEIGMKGERRRGKGHDGLYQGLSTATKD TYDALHMQALPPR | 73 |
| 15 | NKp46-(NKp46-CD2-DAP10) | MGLAFLVLVALVWFLVEDWLSRKRTRERASRASTWEGR RRLNTQTLKRKKQRSRRNDEELETRAHRVATEERGR KPHQIPASTPQNPATSQHPPPPPGHRSQAPSHRPPPPG HRVQHQPQKRPPAPSGTQVHQQKGPPLPRPRVQPKP PHGAAENSLSPSSNLCARPRRSPAQEDGKVYINMPGRG | 74 |
| 16 | CD2-(CD2-CD3ζ) | IYLIIGICGGGSLLMVEVALLVFYITKRKKQRSRRNDEELE TRAHRVATEERGRKPHQIPASTPQNPATSQHPPPPPGHRS QAPSHRPPPPGHRVQHQPQKRPPAPSGTQVHQQKGPPLP RPRVQPKPPHGAAENSLSPSSNRVKFSRSADAPAYQQG QNQLYNELNLGRREEYDVLDKRRGRDPEMGGKPRR KNPQEGLYNELQKDKMAEAYSEIGMKGERRRGKGH DGLYQGLSTATKDTYDALHMQALPPR | 75 |
| 17 | 2B4-(2B4-CD3ζ) | FLVIIVILSALFLGTLACFCVWRRKRKEKQSETSPKEFLTI YEDVKDLKTRRNHEQEQTFPGGGSTIYSMIQSQSSAPTSQ EPAYTLYSLIQPSRKSGSRKRNHSPSFNSTIYEVIGKSQPK AQNPARLSRKELENFDVYSRVKFSRSADAPAYQQGQN QLYNELNLGRREEYDVLDKRRGRDPEMGGKPRRKNP QEGLYNELQKDKMAEAYSEIGMKGERRRGKGHDGL YQGLSTATKDTYDALHMQALPPR | 76 |
| 18 | 2B4-(2B4-FcERIγ) | FLVIIVILSALFLGTLACFCVWRRKRKEKQSETSPKEFLTI YEDVKDLKTRRNHEQEQTFPGGGSTIYSMIQSQSSAPTSQ EPAYTLYSLIQPSRKSGSRKRNHSPSFNSTIYEVIGKSQPK AQNPARLSRKELENFDVYSRLKIQVRKAAITSYEKSDG VYTGLSTRNQETYETLKHEKPPQ | 77 |
| 19 | CS1-(CS1-CD3ζ) | VLLCLLLVPLLLSLFVLGLFLWFLKRERQEEYIEEKKRVD ICRETPNICPHSGENTEYDTIPHTNRTILKEDPANTVYSTV EIPKKMENPHSLLTMPDTPRLFAYENVIRVKFSRSADAP AYQQGQNQLYNELNLGRREEYDVLDKRRGRDPEMG GKPRRKNPQEGLYNELQKDKMAEAYSEIGMKGERR RGKGHDGLYQGLSTATKDTYDALHMQALPPR | 78 |

In some embodiments, the ectodomain can further include a signal peptide or leader sequence and/or a spacer/hinge. In some embodiments, there is a spacer/hinge between the antigen recognition region and the transmembrane domain of the CAR, although in some other embodiments such spacer/hinge is not required. Exemplary N-terminal signal peptides include MALPVTALLLPLALLLHA (SEQ ID NO: 79; CD8asp) or MDFQVQIFSFLLISASVIMSR (SEQ ID NO: 80; IgKsp), or any signal peptide sequence or functional variants thereof known in the art. Exemplary spacers that may be included in a CAR are commonly known in the art, including, but not limited to, IgG4 spacers, CD28 spacers, CD8 spacers, or combinations of more than one spacer. The length of the spacers may also vary, from about 15 amino acids (a.a.) to about 300 a.a, or more. In this application, for ease of description, a spacer of less than around 80 a.a., for example 10-80 a.a., is considered short; a spacer of about 80-180 a.a, is considered medium; and a spacer of more than 180 a.a, is considered long. Non-limiting exemplary spacer peptides include those represented by an amino acid sequence of at least about 80%, about 85%, about 90%, about 95%, about 96%, about 97%, about 98%, or about 99% identity to any of SEQ ID NOs: 81-85. In some embodiments, the spacer peptide comprises an amino acid sequence of at least about 90% identity to any of SEQ ID NOs: 81-85. In some embodiments, the spacer peptide comprises an amino acid sequence of at least about 95% identity to any of SEQ ID NOs: 81-85. In some embodiments, the spacer peptide comprises the amino acid sequence of any of SEQ ID NOs: 81-85.

```
                                            SEQ ID NO: 81
IEVMYPPPYLDNEKSNGTIIHVKGKHLCPSPLFPGPSKP
(39 a.a.)

SEQ ID NO: 82
ESKYGPPCPPCPGGGSSGGGSGGQPREPQVYTLPPSQEE

MTKNQVSLTCLVKGFYPSDIAVEWESNGQPENNYKTTPP

VLDSDGSFFL
(88 a.a.)

SEQ ID NO: 83
ESKYGPPCPPCPAPEFEGGPSVFLFPPKPKDTLMISRTP

EVTCVVVDVSQEDPEVQFNWYVDGVEVHNAKTKPREEQF

QSTYRVVSVLT
(89 a.a.)

SEQ ID NO: 84
ESKYGPPCPPCPGGGSSGGGSGGQPREPQVYTLPPSQEE

MTKNQVSLTCLVKGFYPSDIAVEWESNGQPENNYKTTPP

VLDSDGSFFLYSRLTVDKSRWQEGNVFSCSVMHEALHNH

YTQKSLSLSLGK
(129 a.a.)

SEQ ID NO: 85
ESKYGPPCPPCPAPEFEGGPSVFLFPPKPKDTLMISRTP

EVTCVVVDVSQEDPEVQFNWYVDGVEVHNAKTKPREEQF

QSTYRVVSVLTVLHQDWLNGKEYKCKVSNKGLPSSIEKT

ISKAKGQPREPQVYTLPPSQEEMTKNQVSLTCLVKGFYP

SDIAVEWESNGQPENNYKTTPPVLDSDGSFFLYSRLTVD

KSRWQEGNVFSCSVMHEALHNHYTQKSLSLSLGK
(229 a.a.)
```

In one embodiment, the CAR provided herein comprises a co-stimulatory domain derived from CD28, and a signaling domain comprising the native or modified ITAM1 of CD3ζ, represented by an amino acid sequence having at least about 85%, about 90%, about 95%, about 96%, about 97%, about 98%, or about 99% identity to SEQ ID NO: 63. In some embodiments, the signaling domain comprises an amino acid sequence with at least about 90% identity to SEQ ID NO: 63. In some embodiments, the signaling domain comprises an amino acid sequence with at least about 95% identity to SEQ ID NO: 63. In some embodiments, the signaling domain comprises the amino acid sequence of SEQ ID NO: 63. In a further embodiment, the CAR comprising a co-stimulatory domain derived from CD28, and a native or modified ITAM1 of CD3ζ also comprises a hinge domain (or "spacer") and trans-membrane domain derived from CD28, wherein an scFv may be connected to the transmembrane domain through the hinge, and the CAR comprises an amino acid sequence of at least about 85%, about 90%, about 95%, about 96%, about 97%, about 98%, or about 99;% identity to SEQ ID NO: 86, wherein the spacer may vary in length and sequence. In some embodiments, the CAR comprises an amino acid sequence of at least 80% to SEQ ID NO: 86, wherein the spacer may vary in length and sequence. In some embodiments, the CAR comprises an amino acid sequence of at least 90% to SEQ ID NO: 86, wherein the spacer may vary in length and sequence. In some embodiments, the CAR comprises an amino acid sequence of at least 95% to SEQ ID NO: 86, wherein the spacer may vary in length and sequence. In some embodiments, the CAR comprises the amino acid sequence of SEQ ID NO: 86.

```
                                            SEQ ID NO: 86
ESKYGPPCPPCPGGGSSGGGSGGQPREPQVYTLPPSQEEM

TKNQVSLTCLVKGFYPSDIAVEWESNGQPENNYKTTPPVL

DSDGSFFLYSRLTVDKSRWQEGNVFSCSVMHEALHNHYTQ

KSLSLSLGKMFWVLVVVGGVLACYSLLVTVAFIIFWVRS

KRSRLLHSDYMNMTPRRPGPTRKHYQPYAPPRDFAAYRS

RVKESRSADAPAYQQGQNQLYNELNLGRREEYDVLDKRRG

RDPEMGGKPRRKNPQEGLFNELQKDKMAEAFSEIGMKGER

RRGKGHDGLFQGLSTATKDTEDALHMQALPPR
(spacer-CD28 TM-CD28 Costim-
CD3ζ1XX activation)
```

In another embodiment, the CAR provided herein comprises a transmembrane domain derived from NKG2D, a co-stimulatory domain derived from 2B4, and a signaling domain comprising the native or modified CD3ζ, represented by an amino acid sequence of at least about 85%, about 90%, about 95%, about 96%, about 97%, about 98%, or about 99% identity to SEQ ID NO: 87. In some embodiments, the CAR comprises an amino acid sequence of at least about 90% identity to SEQ ID NO: 87. In some embodiments, the CAR comprises an amino acid sequence of at least about 95% identity to SEQ ID NO: 87. In some embodiments, the CAR comprises the amino acid sequence of SEQ ID NO: 87. Said CAR comprising a transmembrane domain derived from NKG2D, a co-stimulatory domain derived from 2B4, and a signaling domain comprising the native or modified CD3ζ may further comprise a hinge.

```
                                            SEQ ID NO: 87
SNLFVASWIAVMIIFRIGMAVAIFCCFFFPSWRRKRKEKQ

SETSPKEFLTIYEDVKDLKTRRNHEQEQTEPGGGSTIYSM

IQSQSSAPTSQEPAYTLYSLIQPSRKSGSRKRNHSPSENS

TIYEVIGKSQPKAQNPARLSRKELENEDVYSRVKESRSAD

APAYKQGQNQLYNELNLGRREEYDVLDKRRGRDPEMGGKP

RRKNPQEGLYNELQKDKMAEAYSEIGMKGERRRGKGHDGL

YQGLSTATKDTYDALHMQALPPR
(NKG2D TM-2B4-CD3ζ)
```

In one embodiment, the CAR provided herein comprises an amino acid sequence of at least about 85%, about 90%, about 95%, about 96%, about 97%, about 98%, or about 99% identity to SEQ ID NO: 88, wherein the linker in the ectodomain and the spacer between the ectodomain and transmembrane domain may vary in length and sequence. In some embodiments, the CAR comprises an amino acid sequence of at least about 90% identity to SEQ ID NO: 88, wherein the linker in the ectodomain and the spacer between the ectodomain and transmembrane domain may vary in length and sequence. In some embodiments, the CAR comprises an amino acid sequence of at least about 95% identity to SEQ ID NO: 88, wherein the linker in the ectodomain and the spacer between the ectodomain and transmembrane domain may vary in length and sequence. In some embodiments, the CAR comprises the amino acid sequence of SEQ ID NO: 88. In some embodiments, the CAR provided herein recognizes a HER2 antigen specific to cells of solid tumors. In some embodiments, the CAR provided herein recognizes a HER2 antigen of a tumor comprising breast cancer, ovary cancer, endometrium cancer, lung cancer, esophageal cancer, salivary gland cancer, bladder cancer, gastric cancer, colorectal cancer, or head and neck cancer. In yet some other embodiments, the CAR provided herein recognizes a HER2 antigen of a tumor and does not respond, or has a low level of response, to HER2 expressed on non-cancer or normal cells.

SEQ ID NO: 88
EVQLVESGGGLVQPGGSLKLSCAASGFTFSNYGMSWVRQTP
DRRLELVATINNNGGGTYYPDSVKGRFTISRDNAKNTLYL
QMSSLKSEDTAMYYCTSPGLLWDAWGAGTTVTVSSGSTSG
GGSGGGSGGGGSSDVVMTQTPLTLSVSIGQPASISCKSSQ
SLLDSDGRTYLNWLLQRPGQSPKRLIYLVSKLDSGAPDRF
TGSGSGTDFTLKISRVEAEDLGVYYCWQGTHFPQTFGGGT
KLEIK*ESKYGPPCPPCPGGGSSGGGSGGQPREPQVYTIPP*
*SQEEMTKNQVSLTCLVKGFYPSDIAVEWESNGQPENNYKT*
*TPPVLDSDGSFFLYSRLTVDKSRWQEGNVFSCSVMHEALH*
*NHYTQKSLSLSLGKMFWVLVVVGGVLACYSLLVTVAFIIF*
WVRSKRSRLLHSDYMNMTPRRPGPTRKHYQPYAPPRDFAA
YRS*RVKFSRSADAPAYQQGQNQLYNELNLGRREEYDVLDK*
*RRGRDPEMGGKPRRKNPQEGLENELQKDKMAEAFSEIGMK*
*GERRRGKGHDGLFQGLSTATKDTEDALHMQALPPR*
(anti-HER2 scFV[Linker]-*spacer*-CD28 TM-CD28 Costim-CD3ζ1XX *activation*

Non-limiting CAR strategies further include a heterodimeric, conditionally activated CAR through dimerization of a pair of intracellular domains (see for example, U.S. Pat. No. 9,587,020); a split CAR, where homologous recombination of antigen binding, hinge, and endodomains to generate a CAR (see for example, U.S. Pub. No. 2017/0183407); a multi-chain CAR that allows non-covalent linking between two transmembrane domains connected to an antigen binding domain and a signaling domain, respectively (see for example, U.S. Pub. No. 2014/0134142); CARs having bi-specific antigen binding domains (see for example, U.S. Pat. No. 9,447,194), or having a pair of antigen binding domains recognizing the same or different antigens or epitopes (see for example, U.S. Pat. No. 8,409,577), or a tandem CAR (see for example, Hegde et al., *J Clin Invest.* 2016:126(8):3036-3052); an inducible CAR (see for example, U.S. Pub. Nos. 2016/0046700, 2016/0058857, and 2017/0166877); a switchable CAR (see for example, U.S. Pub. No. 2014/0219975); and any other designs known in the art.

In some embodiments, the polynucleotide encoding a CAR as disclosed is operatively linked to an exogenous promoter. The promoters may be inducible, or constitutive, and may be temporal-, tissue- or cell type-specific. Suitable constitutive promoters for methods disclosed herein include, but are not limited to, cytomegalovirus (CMV), elongation factor 1α (EF1α), phosphoglycerate kinase (PGK), hybrid CMV enhancer/chicken β-actin (CAG) and ubiquitin C (UBC) promoters. In one embodiment, the exogenous promoter is CAG. The CAR construct may be introduced into a cell, such as a primary T cell, for expression using plasmid vectors (e.g., pAl-11, pXT1, pRc/CMV, pRc/RSV, pcDNAI/Neo) or viral vectors (e.g. adenovirus vectors, adeno-associated virus vectors, retrovirus vectors, lentivirus vectors, or Sendai virus vectors). Available endonucleases capable of introducing targeted insertion to a cell include, but are not limited to, zinc-finger nucleases (ZFN), transcription activator-like effector nucleases (TALEN), RNA-guided CRISPR (Clustered Regular Interspaced Short Palindromic Repeats) systems.

EXAMPLES

The following examples are offered by way of illustration and not by way of limitation.

Example 1—Design and Functional Profiling of CAR Candidates

Various chimeric antigen receptor (CAR) constructs containing CDRs of a HER2 cancer-specific monoclonal antibody (CasMab) specific for HER2 were designed, transduced, and expressed in a cell model, including primary T cells, suitable for CAR characterization and function determination. The variables in the CAR designs include, but are not limited to, variable region orientation, linker sequence and/or length, spacer sequence and/or length, compatibility with endodomain signaling and co-stimulatory domains, which all directly or indirectly impact the CAR functionality profile including, but not limited to, expression level, specificity and efficacy, which need to be properly defined and adjusted through CAR design.

A group of candidate CARs incorporating spacers of differing length within the ectodomain (e.g., short spacer of about 10 to about 80 amino acids; a medium spacer of more than 80 to about 180 amino acids; or a long spacer of more than 180 amino acids) and/or VH and VL in different orientations were constructed and expressed for cancer antigen specific response analysis. By comparing the cytolytic activity of the distinct CAR constructs targeting the same cancer specific antigen, the following assays were performed to determine which constructs, and more specifically which configurations of ectodomain (i.e., spacer length) and endodomain components confer signaling domain responses specific to binding of the CAR to a HER2 antigen expressed on a cancer cell.

4D5-CAR with a HER2 binding domain derived from a known HER2 antibody, Herceptin, with short spacers (for example, a CD28 hinge that is less than 80 a.a.) and CD28-CD3ζ1XX intracellular signaling domains was used as control for comparison with the candidate HER2-CARs based on novel CasMab antibodies. CasMab214-CAR (abbreviated as 214-CAR or 214 in the figures) with the same short spacer and intracellular signaling domain was designed and constructed based on the CasMab214 antibody VH domain (SEQ ID NO: 89—QVTLKESGPGILQPSQTLS-LTCSFSGFSLSTSGMGVSWIRQPSGKGLEWLAHIFW-DDDKR YNPSLKSRLTISKDTSRNKVFLKITSVDTAD-TATYYCARRVVATDWYFDVWGAGTTVTVS S) and VL domain (SEQ ID NO: 90—DIVLTQSPASLAVSLGQ-RATISCRASESVEYYGTTLMQWYQQKPGQPPKLLI-YAASKVES GVPARFSGSGSGTDFSLNIHPVEEDDVA-MYFCQQSRKVPLTFGAGTKLEL); whereas a CasMab-250-CAR (abbreviated as 250-CAR or 250 in the figures) of the same configuration was designed based on CasMab250 antibody CDRs and VH/VL as disclosed in this application.

Figure 1B:
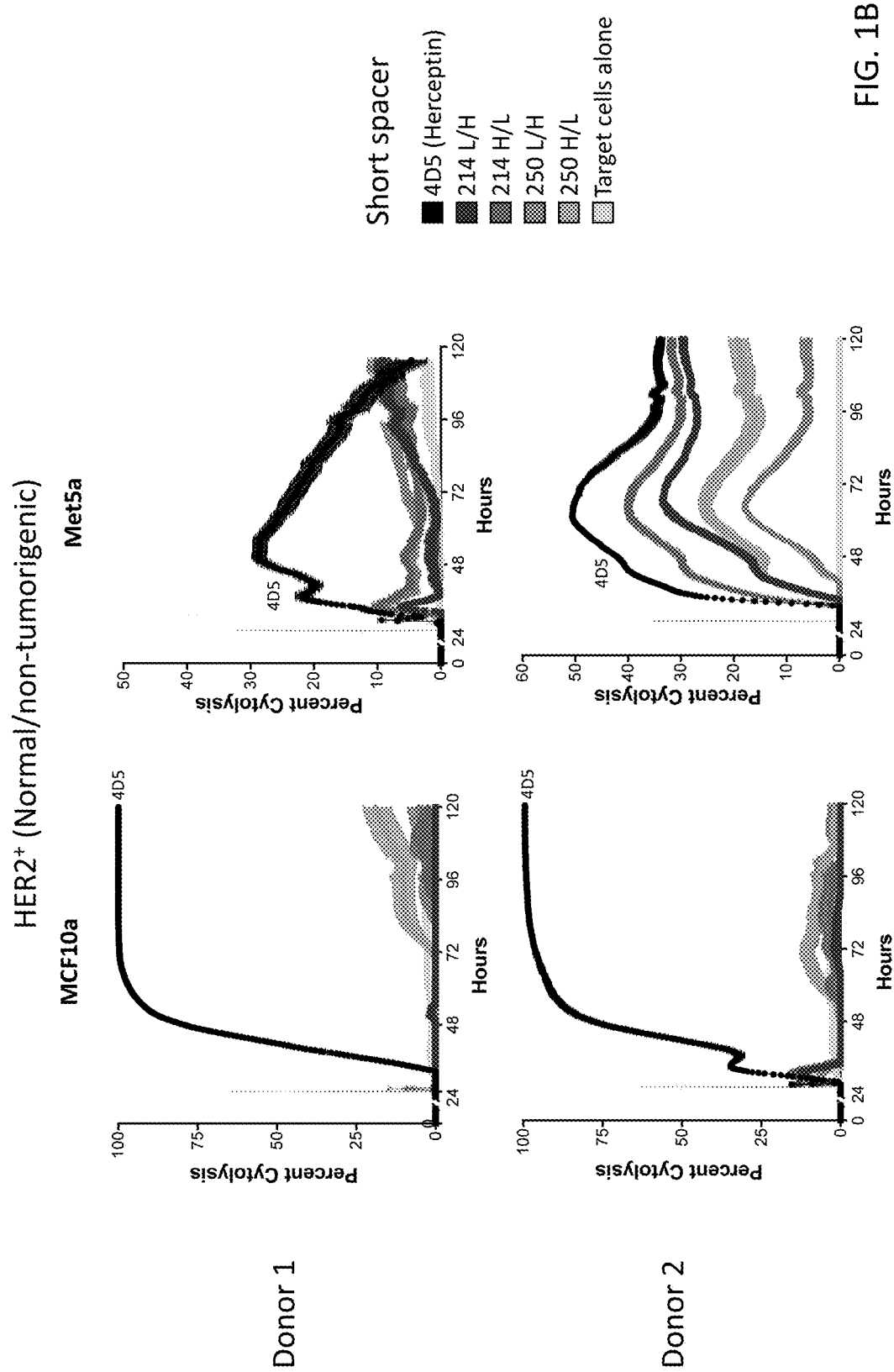

The cytolytic efficacy and specificity of the above CARs was evaluated via xCELLigence™ real time cell analysis, 24 hours after $10^4$ HER2 expressing target cells (SKOV3, SKBR3, MCF10a, or Met5a) were plated, the CAR expressing effector cells were added at a 1:1 effector:target (E:T) ratio for tumor cells SKOV3 and SKBR3 with high HER2 expressing level (HER2$^{High}$) (FIG. 1A), or at a 5:1 E:T ratio for normal/non-tumorigenic HER2 expressing cells MCF10a or Met5a (HER2$^+$) (FIG. 1B). The levels of HER2 expression in the target cells were determined by immunohistochemistry (IHC) staining. The higher the IHC score the higher the expression of the HER2 cell surface antigen. An IHC score of 3+ is labeled as HER2$^{High}$; an IHC score of 2+ is labeled as HER2$^+$, representing a medium HER2 expressor; while an IHC score of 1+ is labeled as HER2$^{Low}$, which represents a low HER2 expressor. Cell indices were monitored, normalized to effector addition, and percent cytolysis was calculated with RTCA Software Pro™.

Figure 4B:
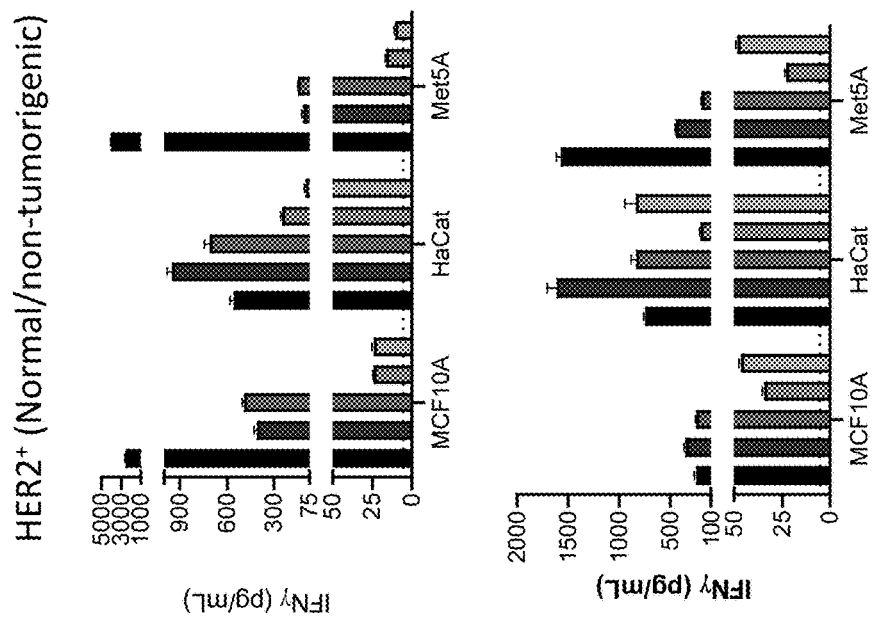
FIGS. 4A and 4B show production of the inflammatory cytokine IFNγ in donor T cells transduced with 4D5-, CasMab214-, or CasMab250-based CARs having a long spacer in response to HER2$^{High}$ tumor cells and HER2$^+$ normal/non-tumorigenic cells.

As shown in FIG. 1A, 4D5-, CasMab214-, and CasMab250-based CAR expressing effector cells all recognized and eliminated the HER2$^{High}$ ovarian (SKOV3) and breast (SKBR3) tumor cell line cells, reaching ~100% percent cytolysis within 48 hours of adding the CAR expressing effector cells. Across all primary donors evaluated, the anti-tumor efficacy through the CasMab214- and CasMab250-based CARs was at least as rapid as, or in most cases preceded the targeting and elimination of tumor lines by up to 12 hours than, donor matched 4D5-based CAR, highlighting the robust anti-tumor potential of CasMab214- and CasMab250-CARs.

For the non-tumorigenic/normal HER2$^+$ cell lines MCF10a (breast) and Met5a (mesothelium), 4D5-CAR expressing donor T cells demonstrated robust cytolytic efficacy, indiscrimitively and rapidly eliminating 100% of normal breast cell line cells (MCF10a) and about 30-50% of normal mesothelium cell line cells (Met5a), indicating a lack of cancer cell targeting specificity of 4D5-CAR based on the HER2 antibody, Herceptin. As such, the 4D5-based HER2-CAR presented an "on-target off-tumor" problem, resulting from a direct attack on normal tissues that have shared expression of the targeted antigen. CasMab214- and CasMab250-based CARs, on the other hand, displayed no cytolytic efficacy against the normal breast MCF10a line, even at an E:T ratio of 5:1, while having efficacy against the HER2 expressing tumorous cell line cells. While a limited level of donor-dependent recognition was observed with normal mesothelial Met5a cells by CasMab214- and CasMab250-based CARs, their cytolytic efficacy was significantly reduced when reacting to non-tumorigenic normal cells compared to that of 4D5-based CAR. Also noted is that although anti-tumor efficacy was largely similar between the cancer cell specific CasMab HER2 antibody based 214- and 250-CARs, CasMab250-CAR demonstrated the least recognition of normal mesothelial Met5a cell lines. Overall, these data demonstrate that CasMab-derived CARs possess robust anti-tumor HER2-targeted efficacy with limited recognition of HER2 on normal/non-tumorigenic cell lines, as compared to the 4D5-CAR based on the widely known and used HER2 antibody, Herceptin.

Figures 2A, 2B:
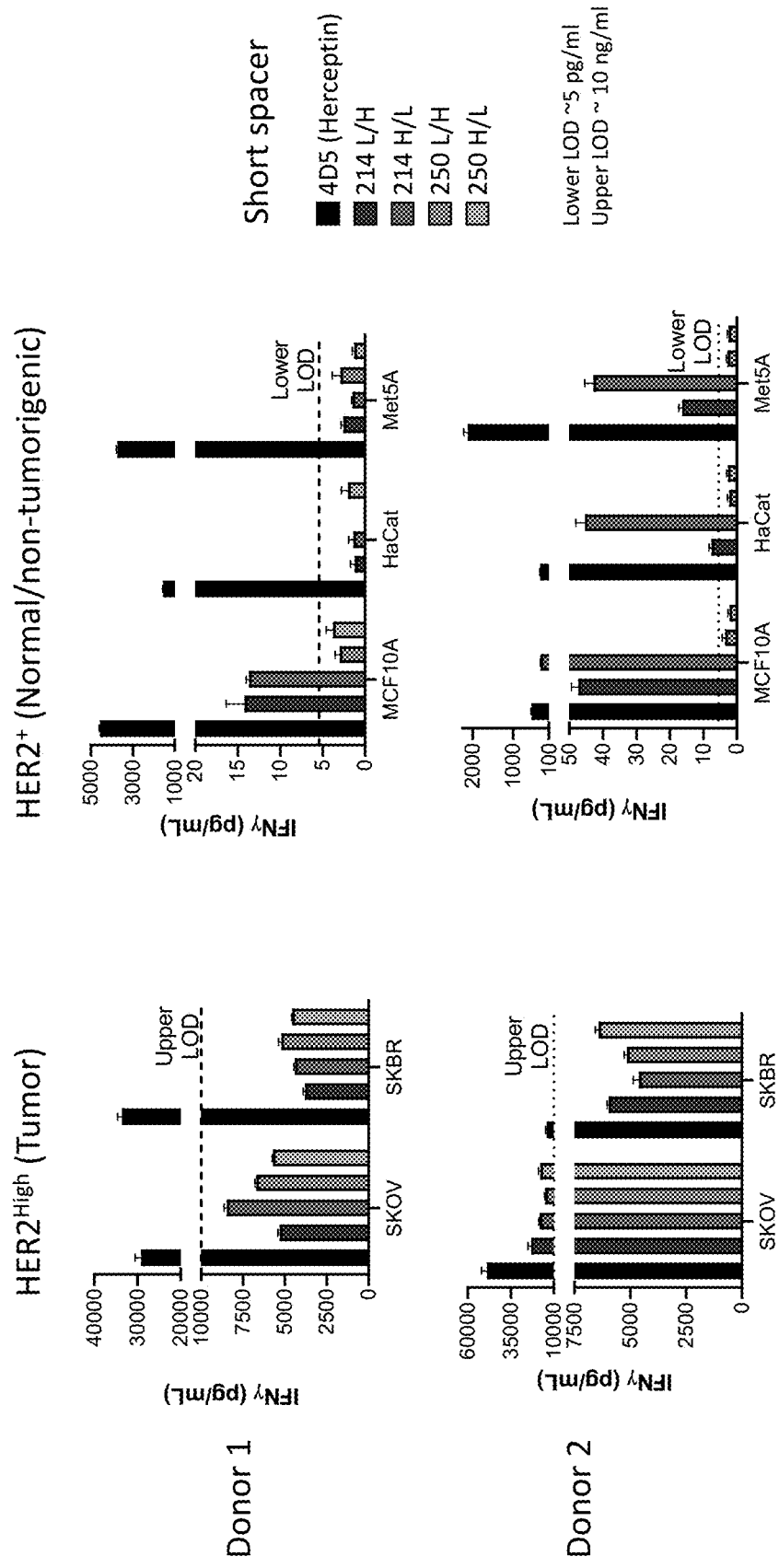
FIGS. 2A and 2B show production of the inflammatory cytokine IFNγ in donor T cells transduced with 4D5-, CasMab214-, or CasMab250-based CARs having a short spacer in response to HER2$^{High}$ tumor cells and HER2$^+$ normal/non-tumorigenic cells.
Figure 3A:
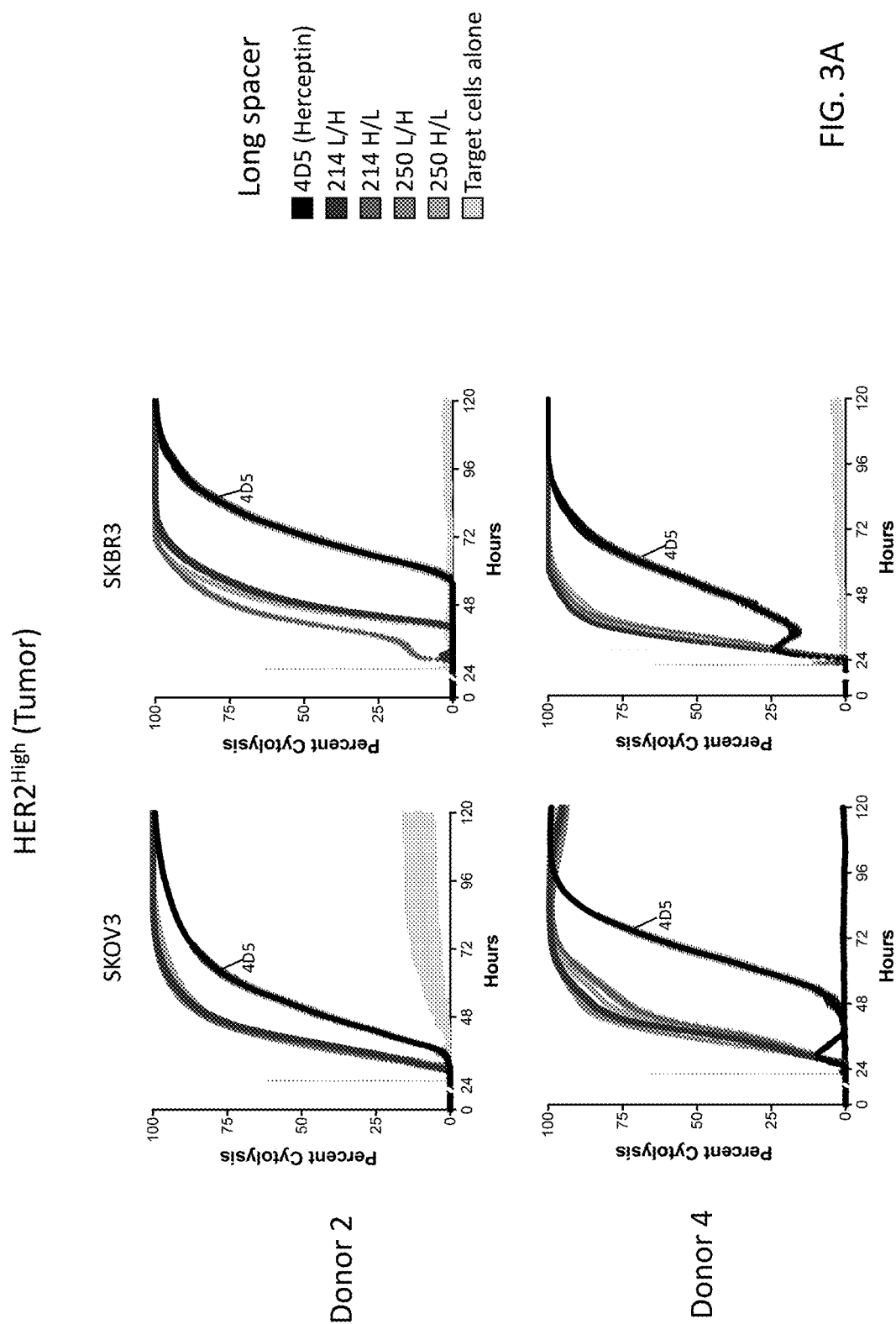
FIGS. 3A and 3B show cytolytic efficacy and specificity of 4D5-, CasMab214-, or CasMab250-based CARs with long spacers against HER2 expressing tumor cells and non-tumorigenic normal cells that express HER2.

Cytokine production in the donor T cells transduced with 4D5-, CasMab214-, or CasMab250-based CARs having a short spacer in response to HER2$^{high}$ tumor cells (SKOV3 and SKBR3; FIG. 2A), and HER2$^+$ normal/non-tumorigenic cells (MCF10a, Met5a and keratinocyte HaCat cell lines; FIG. 2B) were then evaluated. About 24 hours after $5\times10^4$ target cells (SKOV3, SKBR3, MCF10A, HaCat, or Met5a) were plated, the CAR transduced cells were added at a 1:1 E:T ratio. After about 48 hours of co-culturing, supernatants were collected for IFNγ production assessment. For all donors evaluated, the relative production of IFNγ by cells expressing 4D5-CAR targeting either the tumor or non-tumorigenic HER2 expressing cells was substantially greater than that of CasMab214- or CasMab250-based CARs (FIGS. 2A and 2B). Most notably, 4D5-CAR transduced cells also produced about 300 µg/ml to about 4500 µg/ml of IFNγ in response to normal cell co-culture, demonstrating significant reactivity to HER2 expressed on normal cells. CasMab214- and CasMab250-based CAR-T cells, on the other hand, produced substantially less IFNγ across all donors and evaluated normal cell lines, showing much less "on-target off-tumor" effect. CAR-T cells expressing CasMab250-based CAR, in particular, produced no detectable IFNγ (lower than the lower limit of detection of about 5 pg/ml) when exposed to normal HER2-expressing cells, further underscoring the highly specific tumor antigen selectivity of CasMab250-based CAR 4D5-, CasMab214-, or CasMab250-based CARs with long spacers (for example, IgG4 hinge & CH2/3 domains having more than 180 a.a.) were constructed and assessed for cytolytic efficacy and tumor cell specificity using the same methods described above. When against the HER2$^{High}$ ovarian (SKOV3) and breast (SKBR3) tumor cell lines, similar observations were made with the HER2-CARs having long spacers as compared to the CARs having a short spacer. As shown in FIG. 3A, all evaluated long spacer CARs reached maximal efficacy between 72 and 96 hours, with the CasMab214- and CasMab250-based CARs conveying cytolytic efficacy faster than 4D5-CAR both in initiation and in maximization.

Figure 3B:
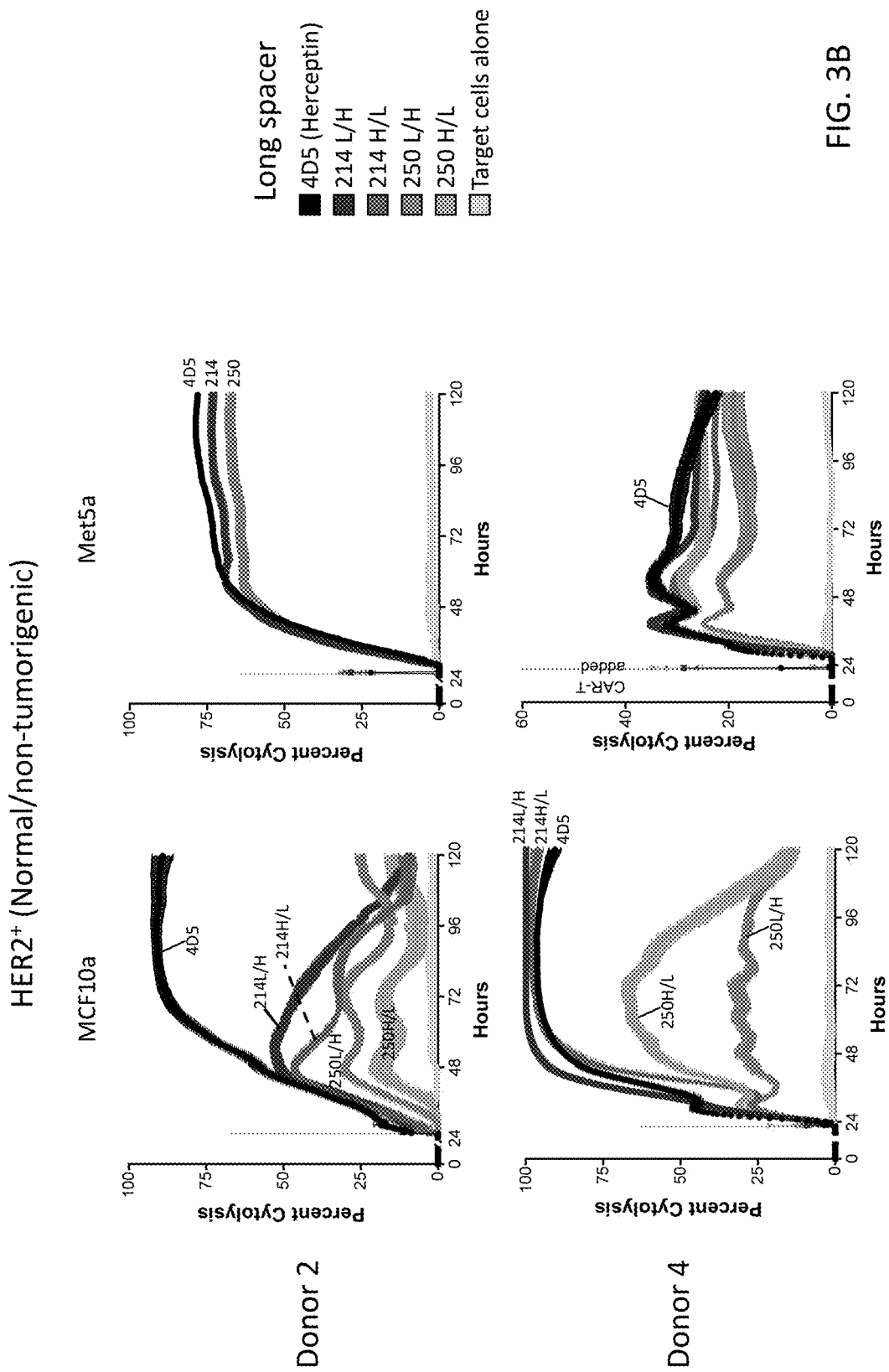

When against the non-tumorigenic/normal HER2$^+$ cell lines MCF10a (breast) and Met5a (mesothelium), the 4D5-CAR with a long spacer demonstrated robust cytolytic efficacy, clearing up to 100% of the normal breast MCF10a and up to 75% of the normal mesothelial Met5a cell lines. For 214- and 250-CARs with a long spacer, although differentials in efficacy and selectivity were observed across donors compared to 4D5, the lengthening of the spacer to a long spacer restored substantial levels of reactivity to HER2 expressing normal/non-tumor cells, see FIG. 3B as compared to FIG. 1B. It is noted, however, even with increased reactivity to normal cells, CasMab250-based CAR still conveys the least amount of cytolytic efficacy across the tested donors. Further, the fact that 4D5-, CasMab214-, and CasMab250-based CARs conveyed no differentials in selectivity on Met5a demonstrate: (i) spacer length is important for CasMab-CAR selectivity of tumor rather than normal HER2$^+$ cells; and (ii) CasMab250-based CAR-T cells demonstrate the least amount of normal cell reactivity across spacer configurations.

Figure 4A:
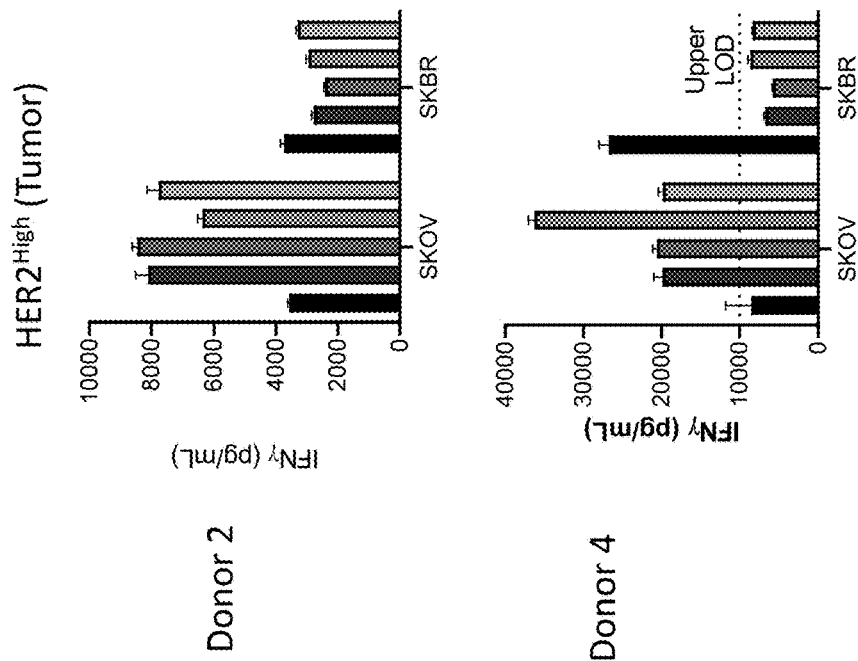

The assay for inflammatory cytokine IFNγ production conveyed by the long spacer CARs in response to HER2-expressing tumor (FIG. 4A) and normal/non-tumorigenic cell lines (FIG. 4B) further confirmed the notion above in terms of the differential effect of spacer length of the HER2-CAR candidates; and more particularly the differential targeting specificity toward non-tumor cells reflected at the level of a CAR, but not at the level of antibody, considering that CasMab214 and CasMab250 were verified antibodies specific for tumor HER2 antigens which were obtained using the same screening method specifically designed for tumor antigens.

Overall, these data demonstrate that (i) CasMab250-based CAR has a tumor selective advantage over similarly configured 4D5- and CasMab214-based CARs, and (ii) spacer length is important for functional properties of CasMab HER2 antibody based CARs, where shorter spacers result in substantially more tumor selectivity than long spacers.

Example 2—Efficacy and Specificity of CasMab250-CAR with Medium Spacers

Since the CasMab250-based CAR has a tumor selective advantage over similarly configured 4D5- and CasMab214-based CARs, this experiment focuses on a comparison of the 250-CAR having a short (less than 80 a.a) or a medium spacer (80-180 a.a.) for any differential functional properties.

4D5- or CasMab250-based CARs with short or medium spacers were evaluated for cytolytic efficacy and tumor specificity using the same methods described herein. As in previous Examples, $10^4$ target cells (SKOV3, SKBR3, BT474 Clone 5, OE19, MCF10a, or Met5a) were plated and allowed to adhere. Approximately 24 hours later, the CAR expressing primary T cells were added at a 1:1 E:T ratio.

Figure 5A:
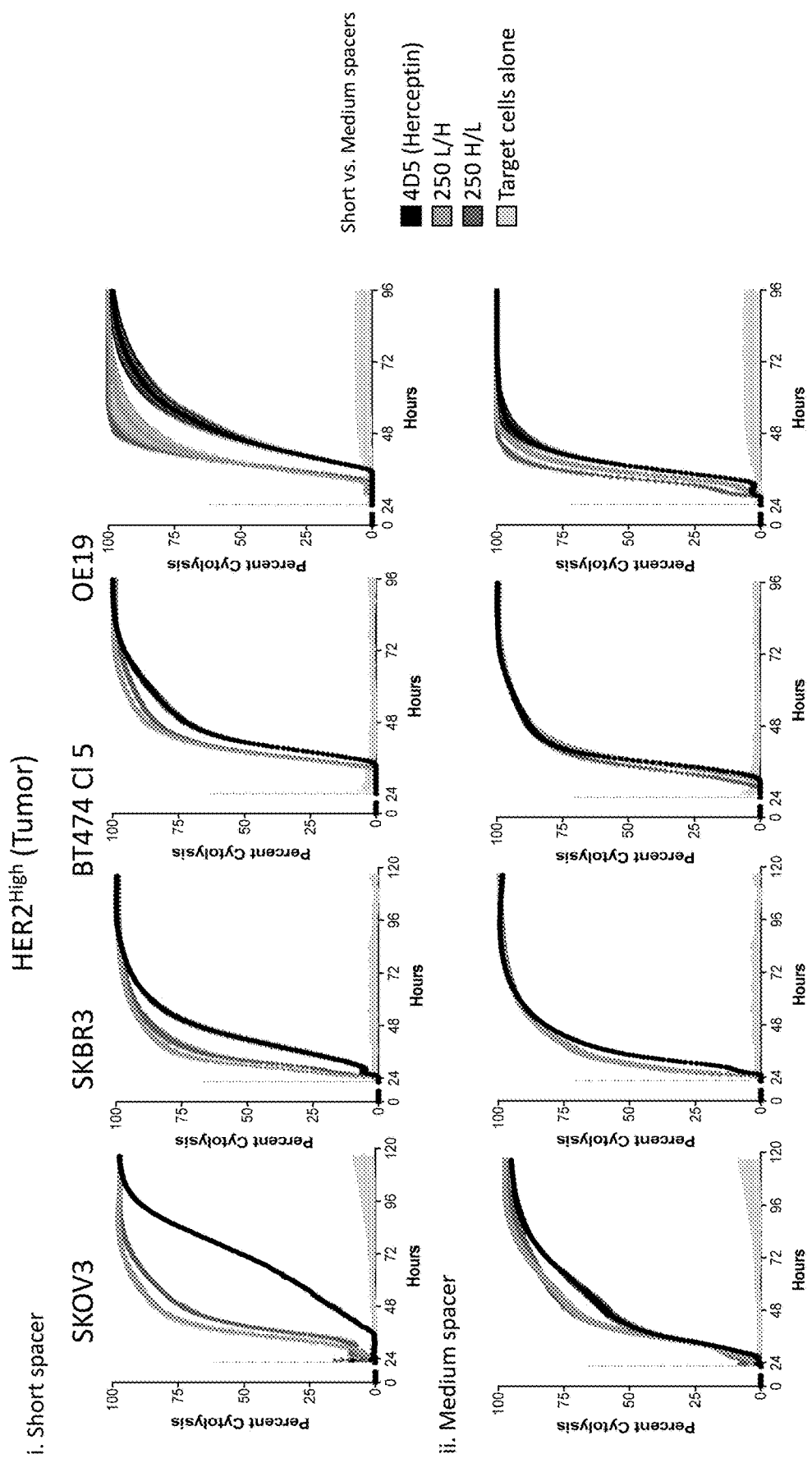
FIGS. 5A and 5B show cytolytic efficacy and tumor specificity of 4D5- or CasMab250-based CARs with short or medium spacers against HER2 expressing tumor cells and non-tumorigenic normal cells that express HER2.

In line with the previous observations, as shown in FIG. 5A, 4D5- and CasMab250-based CARs with short (panel i.) or medium (panel ii.) spacers induced the targeted killing of $HER2^{High}$ SKOV3, SKBR3, BT474 clone 5 (breast), and OE19 (esophageal) tumor cell line cells, reaching maximal cytolytic efficacy within 48 to 96 hours. Moreover, CasMab250-CARs generally induce faster targeted killing than their equivalently configured 4D5-based CAR. Additionally. CasMab250-CARs with medium spacers outperformed those with short spacers across all evaluated $HER2^{High}$ tumor cell lines (FIG. 5A).

Figure 5B:
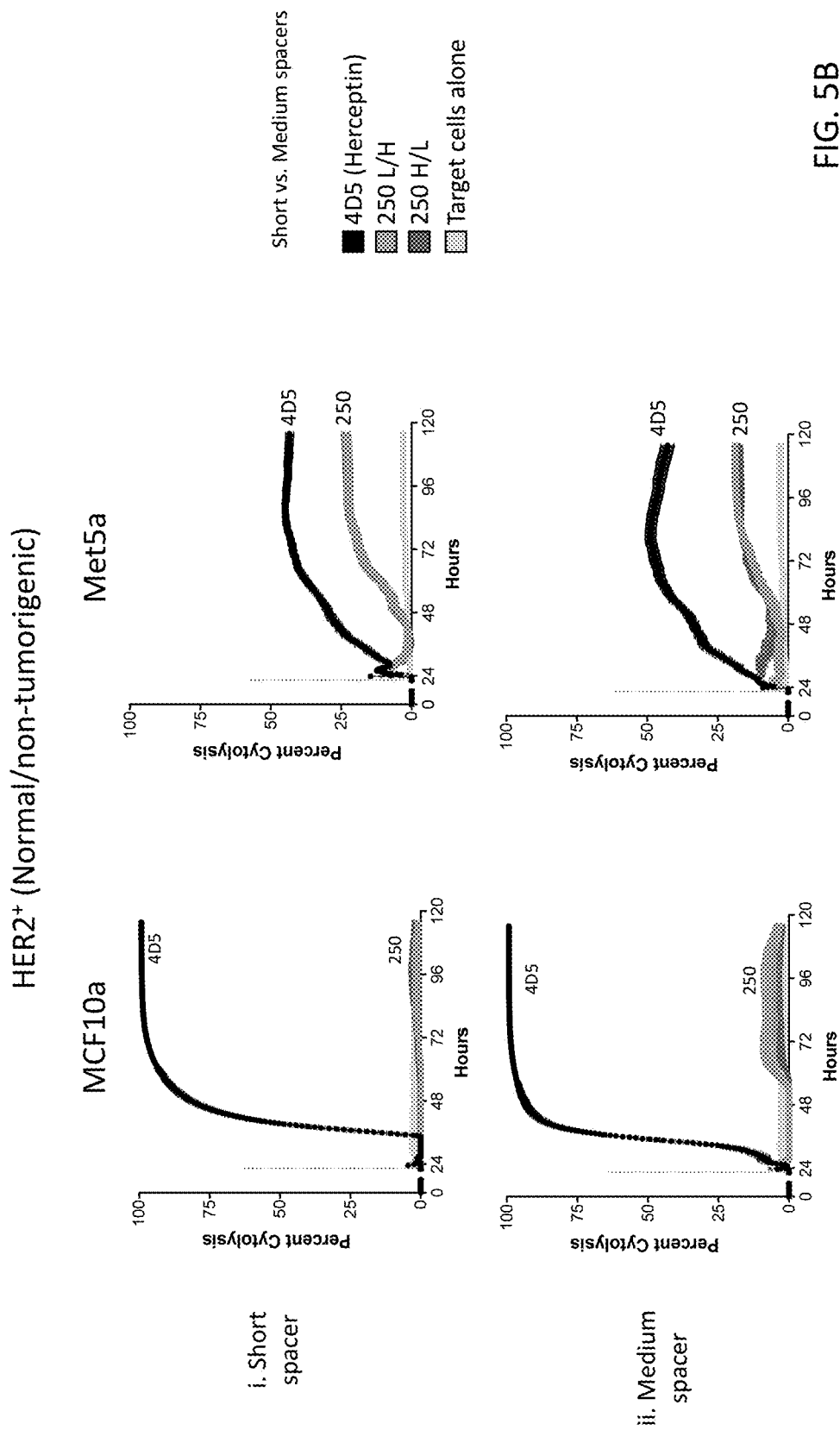

As shown in FIG. 5B, 4D5-based CARs with either short or medium spacers indiscriminately induced high cytotoxicity towards non-tumor/normal HER2 expressing cells. CasMab250-based CARs with either the short or medium spacer configuration, on the other hand, induced no or minimal reactivity to these normal HER2 expressing cells, demonstrating highly selective efficacy against HER2 expressing tumor cells.

Figure 6:
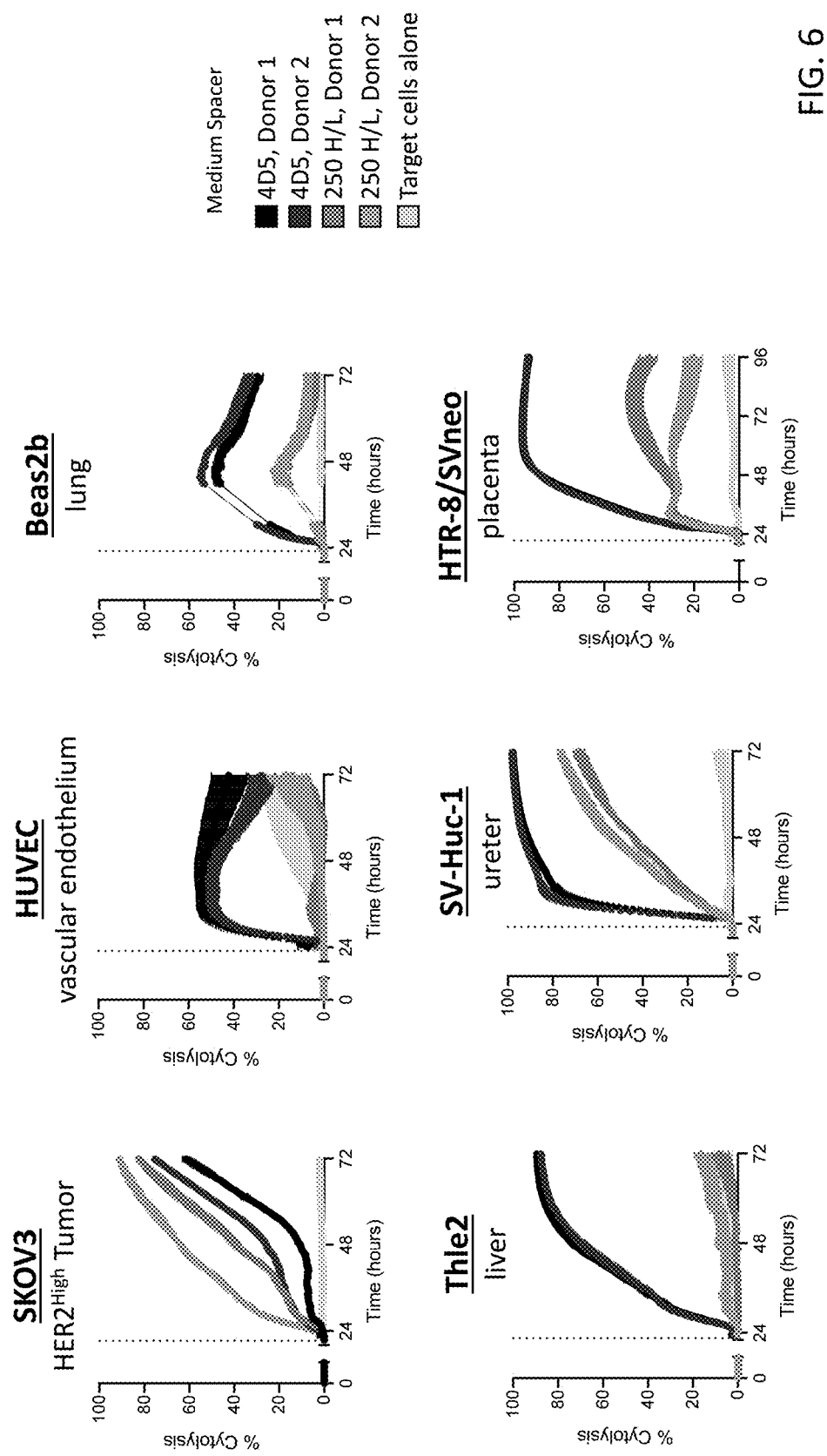
FIG. 6 shows tumor specificity of CasMab250 (H/L)-based CAR having medium spacers towards additional HER2$^{Low/+}$ normal cell lines.

In a separate experiment, the tumor specific efficacy of CasMab250-CAR having a medium spacer and an H/L variable region orientation was further evaluated with additional $HER2^{Low/+}$ normal cell lines (HUVEC, Beas2b, Thle2, SV-Huc-1, and HTR-8/SVneo). A similarly constructed 4D5-CAR was included as control. Target cells (including a HER2 tumor cell line, SKOV3, as a control) were plated. Approximately 24 hours later, the CAR transduced primary T cells were added at a 1:1 E:T ratio. As shown in FIG. 6, CasMab250-CAR (H/L; medium spacer) induced low to no detectable cytoxicity (about 5-40% maximal cytolytic efficacy) across the evaluated normal HER2 expressing cell line cells. These data demonstrate that the CasMab250-based CAR is highly selective for tumor-expressed HER2, rather than non-tumor HER2 (thus presenting the least "on-target off-tumor" problem), and this selectivity extends to a diverse number of HER2 expressing normal/non-tumorigenic cell lines from multiple sources.

Example 3-CAR Intracellular Signaling Domains and CasMab250-CAR Cell Activation

To show CAR cell activation, NFκB reporter Jurkat cells were transduced to express either 4D5- or CasMab250 (H/L)-based CARs with medium spacers (IgG4 hinge & CH3 domain), and CD28-CD3ζ1XX intracellular signaling domains, as described above. Jurkats stably expressing either 4D5- or CasMab250 (H/L)-CARs were co-cultured overnight with $HER2^{High}$ tumor (SKOV3, SKBR3) or $HER2^+$ normal/non-tumorigenic (MCF10a) cell lines. The expressions of GFP (a readout of NFκB and therefore CAR activation) and CD69 (a general activation marker) were assessed via flow cytometry. PMA/Ionomycin and parallel unstimulated Jurkat cell lines served as positive and negative controls, respectively.

Figure 7:
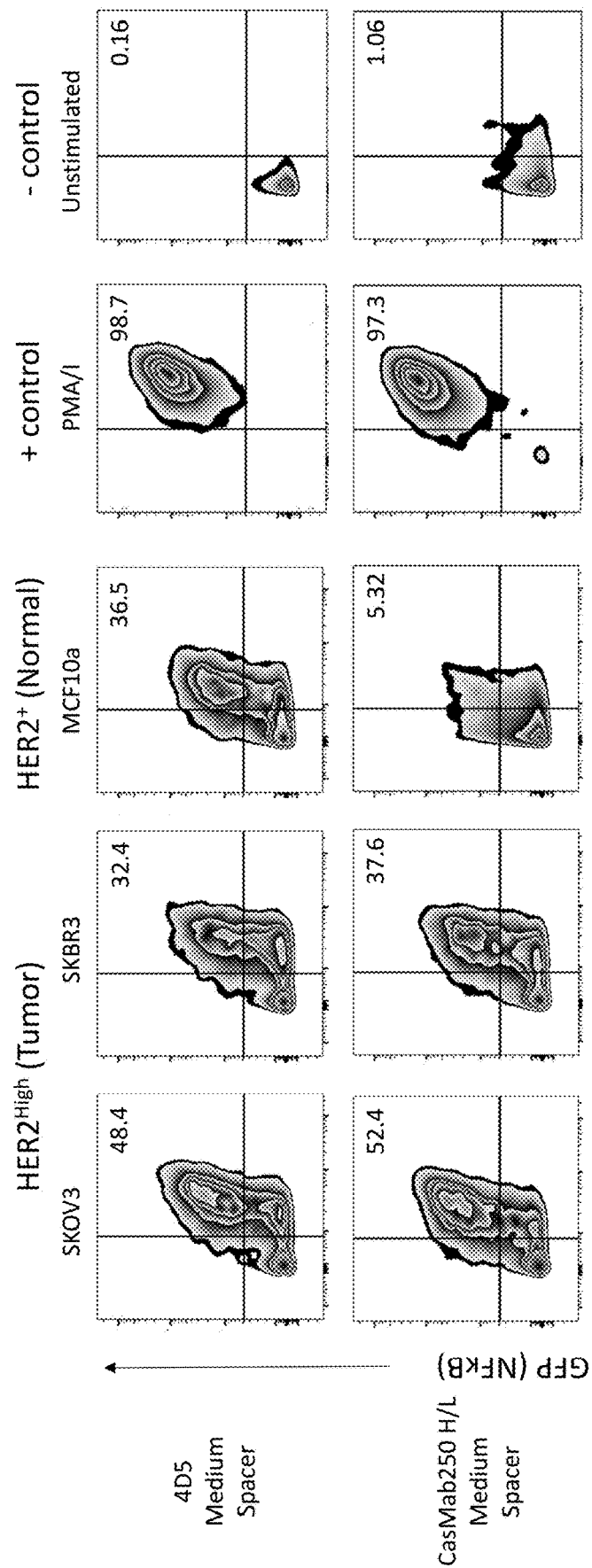
FIG. 7 shows HER2-CAR transduced Jurkat cell were activated in response to HER2$^{High}$ tumor cells and HER2$^+$ normal/non-tumorigenic cells shown by the NFκB reporter marker expression. The HER2-CAR is either 4D5- or CasMab250 (H/L)-based.

As shown in FIG. 7, PMA/Ionomycin (PMA/I) treatment resulted in nearly 100% $GFP^+/CD69^+$ co-expressing cells. Similarly, no CAR-specific cell activation was detected in unstimulated Jurkat reporter lines expressing 4D5- or CasMab250 (H/L)-based CAR (<~1% $GFP^+/CD69^+$). Both 4D5- and CasMab250 (H/L)-CAR expressing Jurkat cells demonstrated specific cell activation following co-culture with SKOV3 or SKBR3 tumor lines ($GFP^+/CD69^+$ about 48-52% for SKOV3 and about 32-38% for SKBR3). Importantly, co-culture of CasMab250 (H/L)-CAR expressing Jurkats with $HER2^+$ normal/non-tumorigenic MCF10a cells induced minimal cell activation (about 5% $GFP^+/CD69^+$), and co-culture of 4D5-CAR expressing Jurkats with MCF10a cells resulted in robust cell activation (about 37% $GFP^+/CD69^+$), which was similar to the cell activation observed under the $HER2^{High}$ SKBR3 tumor cell line. These data further demonstrate that CARs constructed from CasMab250 (H/L) with medium spacers are highly selective and efficacious for tumor-expressed HER2.

Figure 8:
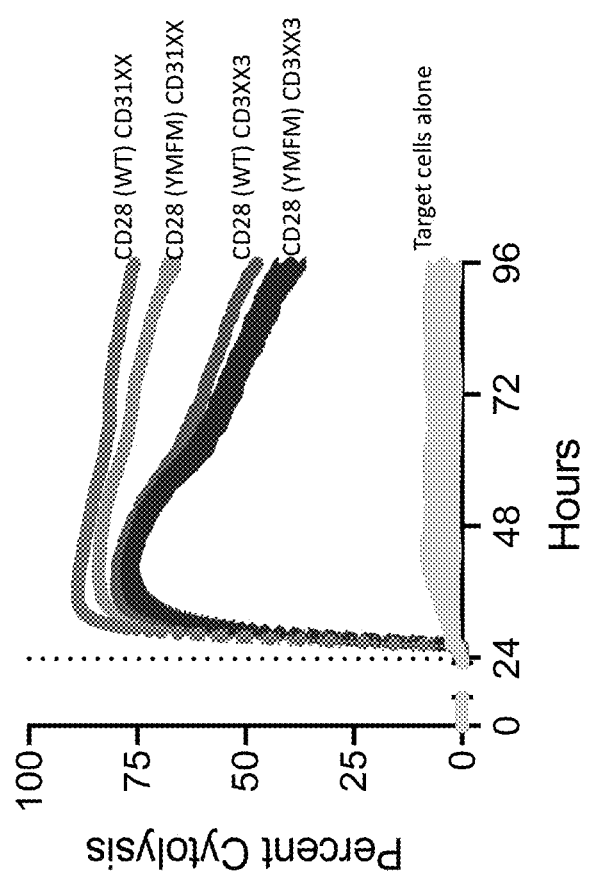
FIG. 8 shows evaluation of multiple intracellular signaling domain configurations alongside the optimized extracellular domain of a CAR based on CasMab250.

In a separate experiment, multiple intracellular signaling domain configurations (from wildtype CD28 or CD28 YMFM mutant, in combination with CD3ζ1XX or CD3ζXX3) were evaluated alongside the optimized extracellular CAR domain of CasMab250 (H/L) ScFv and spacer. CD3ζXX3 is another mutant form of CD3ζ, with two substitutions in ITAM1 (sequence not disclosed), $10^4$ target cells (SKOV3) were plated and allowed to adhere. Approximately 24 hours later, the CAR expressing donor T cells were added at a 1:1 E:T ratio. Cell indices were monitored, normalized to effector addition, and percent cytolysis was calculated with RTCA Software Pro™. As shown in FIG. 8, although all CARs having different intracellular signaling domain configurations exhibited rapid and strong tumor killing, CasMab250-CAR with the CD28-CD3ζ1XX intracellular signaling domain outperformed all other counterparts with ~90% maximal cytolysis, and had better persistence/duration in conveying the cytotoxicity. These data demonstrate that regardless of intracellular signaling domain used, CARs constructed from CasMab250 (H/L) with medium spacers are highly selective and efficacious for tumor-expressed HER2.

One skilled in the art would readily appreciate that the methods, compositions, and products described herein are representative of exemplary embodiments, and not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated as incorporated by reference.

The present disclosure illustratively described herein suitably may be practiced in the absence of any element or elements, limitation or limitations that are not specifically disclosed herein. Thus, for example, in each instance herein any of the terms "comprising," "consisting essentially of,"

and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A chimeric antigen receptor (CAR) comprising:
   (a) an ectodomain comprising an antigen binding domain recognizing a HER2 (human epidermal growth factor receptor 2) antigen, wherein the antigen binding domain comprises:
      (i) a heavy chain variable (VH) domain comprising a heavy chain complementary determining region 1 (H-CDR1) comprising SEQ ID NO: 1 (NYGMS), a heavy chain complementary determining region 2 (H-CDR2) comprising SEQ ID NO: 2 (TINNNGGGTYYPDSVKG), and a heavy chain complementary determining region 3 (H-CDR3) comprising SEQ ID NO: 3 (PGLLWDA); and
      (ii) a light chain variable (VL) domain comprising a light chain complementary determining region 1 (L-CDR1) comprising SEQ ID NO: 4 (KSSQSLL-DSDGRTYLN), a light chain complementary determining region 2 (L-CDR2) comprising SEQ ID NO: 5 (LVSKLDS), and a light chain complementary determining region 3 (L-CDR3) comprising SEQ ID NO: 6 (WQGTHFPQT);
   (b) a transmembrane domain; and
   (c) an endodomain comprising at least one signaling domain;
   wherein the at least one signaling domain responds specifically to binding of the CAR to a HER2 antigen expressed on a cancer cell, thereby generating a cancer antigen specific response.

2. The CAR of claim 1, wherein the antigen binding domain:
(a) comprises a VH domain with at least 80% sequence identity to SEQ ID NO: 7;
(b) comprises a VL domain with at least 80% sequence identity to SEQ ID NO: 8;
(c) comprises a single chain variable fragment (scFV) comprising VH-linker-VL or VL-linker-VH, wherein the linker varies in length and sequence, and optionally wherein the linker has at least 80% sequence identity to SEQ ID NOs: 9-12;
(d) comprises an scFV represented by an amino acid sequence that is of at least about 99%, about 98%, about 96%, about 95%, about 90%, about 85%, or about 80% identity to SEQ ID NO: 13 or SEQ ID NO: 14, wherein each of SEQ ID NOs: 13 and 14 comprises a linker that varies in length and sequence; and/or
(e) is humanized.

3. The CAR of claim 1, wherein the at least one signaling domain comprises:
(a) any one of: 2B4 (Natural killer Cell Receptor 2B4), 4-1BB (Tumor necrosis factor receptor superfamily member 9), CD16 (IgG Fc region Receptor III-A), CD2 (T-cell surface antigen CD2), CD28 (T-cell-specific surface glycoprotein CD28), CD28H (Transmembrane and immunoglobulin domain-containing protein 2), CD3ζ (T-cell surface glycoprotein CD3 zeta chain), DAP10 (Hematopoietic cell signal transducer), DAP12 (TYRO protein tyrosine kinase-binding protein), DNAM1 (CD226 antigen), FcERIγ (High affinity immunoglobulin epsilon receptor subunit gamma), IL21R (Interleukin-21 receptor), IL-2Rβ/IL-15RB (Interleukin-2 receptor subunit beta), IL-2Rγ (Cytokine receptor common subunit gamma), IL-7R (Interleukin-7 receptor subunit alpha), KIR2DS2 (Killer cell immunoglobulin-like receptor 2DS2), NKG2D (NKG2-D type II integral membrane protein), NKp30 (Natural cytotoxicity triggering receptor 3), NKp44 (Natural cytotoxicity triggering receptor 2), NKp46 (Natural cytotoxicity triggering receptor 1), CS1 (SLAM family member 7), and CD8 (T-cell surface glycoprotein CD8 alpha chain);
(b) an amino acid sequence that has at least about 85%, about 90%, about 95%, about 96%, about 97%, about 98%, or about 99% identity to a cytoplasmic domain, or a portion thereof, of 2B4, 4-1BB, CD16, CD2, CD28, CD28H, CD3ζ, CD3ζ1XX, DAP10, DAP12, DNAM1, FcERIγ, IL21R, IL2Rβ (IL15Rβ), IL2Rγ, IL7R, KIR2DS2, NKG2D, NKp30, NKp44, NKp46, CS1, or CD8, represented by SEQ ID NOs: 37-59, respectively; and/or
(c) an amino acid sequence that has at least about 85%, about 90%, about 95%, about 96%, about 97%, about 98%, or about 99% identity to the cytoplasmic domain, or a portion thereof, of 2B4, CD28, CD3ζ, DAP10, NKG2D, CD3ζ1XX, DNAM1, CS1, or combinations thereof.

4. The CAR of claim 3, wherein the endodomain comprises two different signaling domains, and wherein said endodomain domain comprises fused cytoplasmic domains, or portions thereof, in any one of the forms: 2B4-CD3ζ/1XX, 2B4-DNAM1, 2B4-FcERIγ, 2B4-DAP10, CD16-DNAM1, CD16-DAP10, CD16-DAP12, CD2-CD3ζ/1XX, CD2-DNAM1, CD2-FcERIγ, CD2-DAP10, CD28-DNAM1, CD28-FcERIγ, CD28-DAP10, CD28-DAP12, CD28-CD3ζ/1XX, CD28H-CD3ζ/1XX, DAP10-CD3ζ/1XX, DAP10-DAP12, DAP12-CD3ζ/1XX, DAP12-DAP10, DNAM1-CD3ζ/1XX, KIR2DS2-CD3ζ/1XX, KIR2DS2-DAP10, KIR2DS2-2B4, or NKp46-2B4.

5. The CAR of claim 1, wherein the transmembrane domain comprises an amino acid sequence that has at least about 85%, about 90%, about 95%, about 96%, about 97%, about 98%, or about 99% identity to a transmembrane region, or a portion thereof, of:
(a) CD2, CD3δ, CD3ε, CD3γ, CD3ζ, CD4, CD8, CD8a, CD8b, CD16, CD27, CD28, CD28H, CD40, CD84, CD166, 4-1BB, OX40, ICOS, ICAM-1, CTLA4, PD1, LAG3, 2B4, BTLA, DNAM1, DAP10, DAP12, FcERIγ, IL7, IL12, IL15, KIR2DL4, KIR2DS1, KIR2DS2, NKp30, NKp44, NKp46, NKG2C, NKG2D, CS1, or T cell receptor polypeptide;
(b) 2B4, CD2, CD16, CD28, CD28H, CD3ζ, DAP10, DAP12, DNAM1, FcERIγ, KIR2DS2, NKG2D, NKp30, NKp44, NKp46, CS1, or CD8; or
(c) 2B4, CD28, CD28H, DAP10, DNAM1, KIR2DS2, and NKG2D.

6. The CAR of claim 1, wherein the transmembrane domain and its immediately linked signaling domain are from a same protein or from different proteins.

7. The CAR of claim 1, wherein the ectodomain comprises one or more of:
(a) a signal peptide; and/or
(b) a spacer/hinge.

8. The CAR of claim 7, wherein the spacer/hinge comprises
(a) an IgG4 spacer, a CD28 spacers, a CD8 spacer, a CH3 spacer, a CH2/CH3 spacer, or any combination thereof;
(b) a short spacer of about 10 to about 80 amino acids; a medium spacer of more than 80 to about 180 amino acids; or a long spacer of more than 180 amino acids; and/or
(c) an amino acid sequence of at least about 80%, about 85%, about 90%, about 95%, about 96%, about 97%, about 98%, or about 99% identity to any of SEQ ID NOs: 81-85.

9. The CAR of claim 8, wherein the spacer/hinge comprises a medium spacer, wherein the spacer comprises an amino acid sequence of at least about 80%, about 85%, about 90%, about 95%, about 96%, about 97%, about 98%, or about 99% identity to SEQ ID NO: 84.

10. The CAR of claim 1, wherein the CAR comprises an amino acid sequence of at least about 90%, about 95%, about 96%, about 97%, about 98%, or about 99% identity to SEQ ID NO: 88.

11. The CAR of claim 1, wherein the cancer cell is a breast cancer cell, an ovary cancer cell, an endometrium cancer cell, a lung cancer cell, an esophageal cancer cell, a salivary gland cancer cell, a bladder cancer cell, a gastric cancer cell, a colorectal cancer cell, or a head and neck cancer cell.

12. The CAR of claim 1, wherein the at least one signaling domain (i) does not respond to HER2 expressed on non-cancer cells, or (ii) has a lower level of response to HER2 expressed on non-cancer cells as compared to a level of response to a HER2+ cancer cell.

13. The CAR of claim 1, wherein the cancer antigen specific responses comprise cytolysis and cytokine production.

14. The CAR of claim 1, wherein the CAR comprises the VH domain followed by the VL domain in an amino to carboxy direction.

15. A polynucleotide comprising a nucleic acid sequence which encodes a CAR according to claim 1.

16. A vector comprising the polynucleotide according to claim 15.

* * * * *

```
                           SEQUENCE LISTING

Sequence total quantity: 90
SEQ ID NO: 1            moltype = AA  length = 5
FEATURE                 Location/Qualifiers
source                  1..5
                        mol_type = protein
                        organism = synthetic construct
SEQUENCE: 1
NYGMS                                                                    5

SEQ ID NO: 2            moltype = AA  length = 17
FEATURE                 Location/Qualifiers
source                  1..17
                        mol_type = protein
                        organism = synthetic construct
SEQUENCE: 2
TINNNGGGTY YPDSVKG                                                       17

SEQ ID NO: 3            moltype = AA  length = 7
FEATURE                 Location/Qualifiers
source                  1..7
                        mol_type = protein
                        organism = synthetic construct
SEQUENCE: 3
PGLLWDA                                                                  7

SEQ ID NO: 4            moltype = AA  length = 16
FEATURE                 Location/Qualifiers
source                  1..16
                        mol_type = protein
                        organism = synthetic construct
SEQUENCE: 4
KSSQSLLDSD GRTYLN                                                        16

SEQ ID NO: 5            moltype = AA  length = 7
FEATURE                 Location/Qualifiers
source                  1..7
                        mol_type = protein
                        organism = synthetic construct
SEQUENCE: 5
LVSKLDS                                                                  7

SEQ ID NO: 6            moltype = AA  length = 9
FEATURE                 Location/Qualifiers
source                  1..9
                        mol_type = protein
                        organism = synthetic construct
SEQUENCE: 6
WQGTHFPQT                                                                9

SEQ ID NO: 7            moltype = AA  length = 116
FEATURE                 Location/Qualifiers
source                  1..116
                        mol_type = protein
                        organism = synthetic construct
SEQUENCE: 7
EVQLVESGGG LVQPGGSLKL SCAASGFTFS NYGMSWVRQT PDRRLELVAT INNNGGGTYY         60
PDSVKGRFTI SRDNAKNTLY LQMSSLKSED TAMYYCTSPG LLWDAWGAGT TVTVSS             116

SEQ ID NO: 8            moltype = AA  length = 112
FEATURE                 Location/Qualifiers
source                  1..112
                        mol_type = protein
                        organism = synthetic construct
SEQUENCE: 8
DVVMTQTPLT LSVSIGQPAS ISCKSSQSLL DSDGRTYLNW LLQRPGQSPK RLIYLVSKLD         60
SGAPDRFTGS GSGTDFTLKI SRVEAEDLGV YYCWQGTHFP QTFGGGTKLE IK                 112
```

```
SEQ ID NO: 9                 moltype = AA  length = 18
FEATURE                      Location/Qualifiers
source                       1..18
                             mol_type = protein
                             organism = synthetic construct
SEQUENCE: 9
GSTSGGGSGG GSGGGGSS                                                         18

SEQ ID NO: 10                moltype = AA  length = 18
FEATURE                      Location/Qualifiers
source                       1..18
                             mol_type = protein
                             organism = synthetic construct
SEQUENCE: 10
GSTSGSGKPG SGEGSTKG                                                         18

SEQ ID NO: 11                moltype = AA  length = 17
FEATURE                      Location/Qualifiers
source                       1..17
                             mol_type = protein
                             organism = synthetic construct
SEQUENCE: 11
SSGGGGSGGG GSGGGGS                                                          17

SEQ ID NO: 12                moltype = AA  length = 15
FEATURE                      Location/Qualifiers
source                       1..15
                             mol_type = protein
                             organism = synthetic construct
SEQUENCE: 12
GGGGSGGGGS GGGGS                                                            15

SEQ ID NO: 13                moltype = AA  length = 246
FEATURE                      Location/Qualifiers
source                       1..246
                             mol_type = protein
                             organism = synthetic construct
SEQUENCE: 13
EVQLVESGGG LVQPGGSLKL SCAASGFTFS NYGMSWVRQT PDRRLELVAT INNNGGGTYY           60
PDSVKGRFTI SRDNAKNTLY LQMSSLKSED TAMYYCTSPG LLWDAWGAGT TVTVSSGSTS          120
GGGSGGGSGG GGSSDVVMTQ TPLTLSVSIG QPASISCKSS QSLLDSDGRT YLNWLLQRPG          180
QSPKRLIYLV SKLDSGAPDR FTGSGSGTDF TLKISRVEAE DLGVYYCWQG THFPQTFGGG          240
TKLEIK                                                                     246

SEQ ID NO: 14                moltype = AA  length = 246
FEATURE                      Location/Qualifiers
source                       1..246
                             mol_type = protein
                             organism = synthetic construct
SEQUENCE: 14
DVVMTQTPLT LSVSIGQPAS ISCKSSQSLL DSDGRTYLNW LLQRPGQSPK RLIYLVSKLD           60
SGAPDRFTGS GSGTDFTLKI SRVEAEDLGV YYCWQGTHFP QTFGGGTKLE IKGSTSGGGS          120
GGGSGGGGSS EVQLVESGGG LVQPGGSLKL SCAASGFTFS NYGMSWVRQT PDRRLELVAT          180
INNNGGGTYY PDSVKGRFTI SRDNAKNTLY LQMSSLKSED TAMYYCTSPG LLWDAWGAGT          240
TVTVSS                                                                     246

SEQ ID NO: 15                moltype = AA  length = 21
FEATURE                      Location/Qualifiers
source                       1..21
                             mol_type = protein
                             organism = synthetic construct
SEQUENCE: 15
FLVIIVILSA LFLGTLACFC V                                                     21

SEQ ID NO: 16                moltype = AA  length = 27
FEATURE                      Location/Qualifiers
source                       1..27
                             mol_type = protein
                             organism = synthetic construct
SEQUENCE: 16
IISFFLALTS TALLFLLFFL TLRFSVV                                               27

SEQ ID NO: 17                moltype = AA  length = 31
FEATURE                      Location/Qualifiers
source                       1..31
                             mol_type = protein
                             organism = synthetic construct
SEQUENCE: 17
VSFCLVMVLL FAVDTGLYFS VKTNIRSSTR D                                          31
```

```
SEQ ID NO: 18          moltype = AA   length = 96
FEATURE                Location/Qualifiers
source                 1..96
                       mol_type = protein
                       organism = synthetic construct
SEQUENCE: 18
IYLIIGICGG GSLLMVFVAL LVFYITKRKK QRSRRNDEEL ETRAHRVATE ERGRKPHQIP   60
ASTPQNPATS QHPPPPPGHR SQAPSHRPPP PGHRVQ                             96

SEQ ID NO: 19          moltype = AA   length = 27
FEATURE                Location/Qualifiers
source                 1..27
                       mol_type = protein
                       organism = synthetic construct
SEQUENCE: 19
FWVLVVVGGV LACYSLLVTV AFIIFWV                                       27

SEQ ID NO: 20          moltype = AA   length = 21
FEATURE                Location/Qualifiers
source                 1..21
                       mol_type = protein
                       organism = synthetic construct
SEQUENCE: 20
FLFVLLGVGS MGVAAIVWGA W                                             21

SEQ ID NO: 21          moltype = AA   length = 21
FEATURE                Location/Qualifiers
source                 1..21
                       mol_type = protein
                       organism = synthetic construct
SEQUENCE: 21
LCYLLDGILF IYGVILTALF L                                             21

SEQ ID NO: 22          moltype = AA   length = 21
FEATURE                Location/Qualifiers
source                 1..21
                       mol_type = protein
                       organism = synthetic construct
SEQUENCE: 22
LLAGLVAADA VASLLIVGAV F                                             21

SEQ ID NO: 23          moltype = AA   length = 21
FEATURE                Location/Qualifiers
source                 1..21
                       mol_type = protein
                       organism = synthetic construct
SEQUENCE: 23
GVLAGIVMGD LVLTVLIALA V                                             21

SEQ ID NO: 24          moltype = AA   length = 21
FEATURE                Location/Qualifiers
source                 1..21
                       mol_type = protein
                       organism = synthetic construct
SEQUENCE: 24
GGTVLLLLFV ISITTIIVIF L                                             21

SEQ ID NO: 25          moltype = AA   length = 20
FEATURE                Location/Qualifiers
source                 1..20
                       mol_type = protein
                       organism = synthetic construct
SEQUENCE: 25
CYILDAILFL YGIVLTLLYC                                               20

SEQ ID NO: 26          moltype = AA   length = 21
FEATURE                Location/Qualifiers
source                 1..21
                       mol_type = protein
                       organism = synthetic construct
SEQUENCE: 26
GWNPHLLLLL LLVIVFIPAF W                                             21

SEQ ID NO: 27          moltype = AA   length = 25
FEATURE                Location/Qualifiers
source                 1..25
                       mol_type = protein
                       organism = synthetic construct
```

```
SEQUENCE: 27
IPWLGHLLVG LSGAFGFIIL VYLLI                                             25

SEQ ID NO: 28          moltype = AA   length = 21
FEATURE                Location/Qualifiers
source                 1..21
                       mol_type = protein
                       organism = synthetic construct
SEQUENCE: 28
VVISVGSMGL IISLLCVYFW L                                                 21

SEQ ID NO: 29          moltype = AA   length = 25
FEATURE                Location/Qualifiers
source                 1..25
                       mol_type = protein
                       organism = synthetic construct
SEQUENCE: 29
PILLTISILS FFSVALLVIL ACVLW                                             25

SEQ ID NO: 30          moltype = AA   length = 20
FEATURE                Location/Qualifiers
source                 1..20
                       mol_type = protein
                       organism = synthetic construct
SEQUENCE: 30
VLIGTSVVKI PFTILLFFLL                                                   20

SEQ ID NO: 31          moltype = AA   length = 21
FEATURE                Location/Qualifiers
source                 1..21
                       mol_type = protein
                       organism = synthetic construct
SEQUENCE: 31
PFFFCCFIAV AMGIRFIIMV A                                                 21

SEQ ID NO: 32          moltype = AA   length = 21
FEATURE                Location/Qualifiers
source                 1..21
                       mol_type = protein
                       organism = synthetic construct
SEQUENCE: 32
AGTVLLLRAG FYAVSFLSVA V                                                 21

SEQ ID NO: 33          moltype = AA   length = 21
FEATURE                Location/Qualifiers
source                 1..21
                       mol_type = protein
                       organism = synthetic construct
SEQUENCE: 33
LVPVFCGLLV AKSLVLSALL V                                                 21

SEQ ID NO: 34          moltype = AA   length = 20
FEATURE                Location/Qualifiers
source                 1..20
                       mol_type = protein
                       organism = synthetic construct
SEQUENCE: 34
GLAFLVLVAL VWFLVEDWLS                                                   20

SEQ ID NO: 35          moltype = AA   length = 21
FEATURE                Location/Qualifiers
source                 1..21
                       mol_type = protein
                       organism = synthetic construct
SEQUENCE: 35
VLLCLLLVPL LLSLFVLGLF L                                                 21

SEQ ID NO: 36          moltype = AA   length = 11
FEATURE                Location/Qualifiers
source                 1..11
                       mol_type = protein
                       organism = synthetic construct
SEQUENCE: 36
IYIWAPLAGT C                                                            11

SEQ ID NO: 37          moltype = AA   length = 120
FEATURE                Location/Qualifiers
source                 1..120
                       mol_type = protein
```

```
                        organism = synthetic construct
SEQUENCE: 37
WRRKRKEKQS ETSPKEFLTI YEDVKDLKTR RNHEQEQTFP GGGSTIYSMI QSQSSAPTSQ    60
EPAYTLYSLI QPSRKSGSRK RNHSPSFNST IYEVIGKSQP KAQNPARLSR KELENFDVYS   120

SEQ ID NO: 38           moltype = AA   length = 42
FEATURE                 Location/Qualifiers
source                  1..42
                        mol_type = protein
                        organism = synthetic construct
SEQUENCE: 38
KRGRKKLLYI FKQPFMRPVQ TTQEEDGCSC RFPEEEEGGC EL                       42

SEQ ID NO: 39           moltype = AA   length = 15
FEATURE                 Location/Qualifiers
source                  1..15
                        mol_type = protein
                        organism = synthetic construct
SEQUENCE: 39
WKDHKFKWRK DPQDK                                                     15

SEQ ID NO: 40           moltype = AA   length = 46
FEATURE                 Location/Qualifiers
source                  1..46
                        mol_type = protein
                        organism = synthetic construct
SEQUENCE: 40
HQPQKRPPAP SGTQVHQQKG PPLPRPRVQP KPPHGAAENS LSPSSN                   46

SEQ ID NO: 41           moltype = AA   length = 41
FEATURE                 Location/Qualifiers
source                  1..41
                        mol_type = protein
                        organism = synthetic construct
SEQUENCE: 41
RSKRSRLLHS DYMNMTPRRP GPTRKHYQPY APPRDFAAYR S                        41

SEQ ID NO: 42           moltype = AA   length = 111
FEATURE                 Location/Qualifiers
source                  1..111
                        mol_type = protein
                        organism = synthetic construct
SEQUENCE: 42
FWGRRSCQQR DSGNSPGNAF YSNVLYRPRG APKKSEDCSG EGKDQRGQSI YSTSFPQPAP    60
RQPHLASRPC PSPRPCPSPR PGHPVSMVRV SPRPSPTQQP RPKGFPKVGE E            111

SEQ ID NO: 43           moltype = AA   length = 113
FEATURE                 Location/Qualifiers
source                  1..113
                        mol_type = protein
                        organism = synthetic construct
SEQUENCE: 43
RVKFSRSADA PAYQQGQNQL YNELNLGRRE EYDVLDKRRG RDPEMGGKPQ RRKNPQEGLY    60
NELQKDKMAE AYSEIGMKGE RRRGKGHDGL YQGLSTATKD TYDALHMQAL PPR          113

SEQ ID NO: 44           moltype = AA   length = 112
FEATURE                 Location/Qualifiers
source                  1..112
                        mol_type = protein
                        organism = synthetic construct
SEQUENCE: 44
RVKFSRSADA PAYQQGQNQL YNELNLGRRE EYDVLDKRRG RDPEMGGKPR RKNPQEGLFN    60
ELQKDKMAEA FSEIGMKGER RRGKGHDGLF QGLSTATKDT FDALHMQALP PR           112

SEQ ID NO: 45           moltype = AA   length = 24
FEATURE                 Location/Qualifiers
source                  1..24
                        mol_type = protein
                        organism = synthetic construct
SEQUENCE: 45
LCARPRRSPA QEDGKVYINM PGRG                                           24

SEQ ID NO: 46           moltype = AA   length = 52
FEATURE                 Location/Qualifiers
source                  1..52
                        mol_type = protein
                        organism = synthetic construct
SEQUENCE: 46
YFLGRLVPRG RGAAEAATRK QRITETESPY QELQGQRSDV YSDLNTQRPY YK            52
```

```
SEQ ID NO: 47           moltype = AA  length = 61
FEATURE                 Location/Qualifiers
source                  1..61
                        mol_type = protein
                        organism = synthetic construct
SEQUENCE: 47
NRRRRRERRD LFTESWDTQK APNNYRSPIS TSQPTNQSMD DTREDIYVNY PTFSRRPKTR    60
V                                                                   61

SEQ ID NO: 48           moltype = AA  length = 42
FEATURE                 Location/Qualifiers
source                  1..42
                        mol_type = protein
                        organism = synthetic construct
SEQUENCE: 48
RLKIQVRKAA ITSYEKSDGV YTGLSTRNQE TYETLKHEKP PQ                       42

SEQ ID NO: 49           moltype = AA  length = 285
FEATURE                 Location/Qualifiers
source                  1..285
                        mol_type = protein
                        organism = synthetic construct
SEQUENCE: 49
SLKTHPLWRL WKKIWAVPSP ERFFMPLYKG CSGDFKKWVG APFTGSSLEL GPWSPEVPST    60
LEVYSCHPPR SPAKRLQLTE LQEPAELVES DGVPKPSFWP TAQNSGGSAY SEERDRPYGL   120
VSIDTVTVLD AEGPCTWPCS CEDDGYPALD LDAGLEPSPG LEDPLLDAGT TVLSCGCVSA   180
GSPGLGGPLG SLLDRLKPPL ADGEDWAGGL PWGGRSPGGV SESEAGSPLA GLDMDTFDSG   240
FVGSDCSSPV ECDFTSPGDE GPPRSYLRQW VVIPPPLSSP GPQAS                   285

SEQ ID NO: 50           moltype = AA  length = 286
FEATURE                 Location/Qualifiers
source                  1..286
                        mol_type = protein
                        organism = synthetic construct
SEQUENCE: 50
NCRNTGPWLK KVLKCNTPDP SKFFSQLSSE HGGDVQKWLS SPFPSSSFSP GGLAPEISPL    60
EVLERDKVTQ LLLQQDKVPE PASLSSNHSL TSCFTNQGYF FPHLPDALEI EACQVYFTYD   120
PYSEEDPDEG VAGAPTGSSP QPLQPLSGED DAYCTFPSRD DLLLFSPSLL GGPSPPSTAP   180
GGSGAGEERM PPSLQERVPR DWDPQPLGPP TPGVPDLVDF QPPPELVLRE AGEEVPDAGP   240
REGVSFPWSR PPGQGEFRAL NARLPLNTDA YLSLQELQGQ DPTHLV                  286

SEQ ID NO: 51           moltype = AA  length = 86
FEATURE                 Location/Qualifiers
source                  1..86
                        mol_type = protein
                        organism = synthetic construct
SEQUENCE: 51
ERTMPRIPTL KNLEDLVTEY HGNFSAWSGV SKGLAESLQP DYSERLCLVS EIPPKGGALG    60
EGPGASPCNQ HSPYWAPPCY TLKPET                                        86

SEQ ID NO: 52           moltype = AA  length = 195
FEATURE                 Location/Qualifiers
source                  1..195
                        mol_type = protein
                        organism = synthetic construct
SEQUENCE: 52
KKRIKPIVWP SLPDHKKTLE HLCKKPRKNL NVSFNPESFL DCQIHRVDDI QARDEVEGFL    60
QDTFPQQLEE SEKQRLGGDV QSPNCPSEDV VITPESFGRD SSLTCLAGNV SACDAPILSS   120
SRSLDCRESG KNGPHVYQDL LLSLGTTNST LPPPFSLQSG ILTLNPVAQG QPILTSLGSN   180
QEEAYVTMSS FYQNQ                                                   195

SEQ ID NO: 53           moltype = AA  length = 39
FEATURE                 Location/Qualifiers
source                  1..39
                        mol_type = protein
                        organism = synthetic construct
SEQUENCE: 53
HRWCSNKKNA AVMDQEPAGN RTVNSEDSDE QDHQEVSYA                           39

SEQ ID NO: 54           moltype = AA  length = 144
FEATURE                 Location/Qualifiers
source                  1..144
                        mol_type = protein
                        organism = synthetic construct
SEQUENCE: 54
IWSAVFLNSL FNQEVQIPLT ESYCGPCPKN WICYKNNCYQ FFDESKNWYE SQASCMSQNA    60
SLLKVYSKED QDLLKLVKSY HWMGLVHIPT NGSWQWEDGS ILSPNLLTII EMQKGDCALY   120
ASSFKGYIEN CSTPNTYICM QRTV                                         144
```

```
SEQ ID NO: 55            moltype = AA   length = 45
FEATURE                  Location/Qualifiers
source                   1..45
                         mol_type = protein
                         organism = synthetic construct
SEQUENCE: 55
GSTVYYQGKC LTWKGPRRQL PAVVPAPLPP PCGSSAHLLP PVPGG                    45

SEQ ID NO: 56            moltype = AA   length = 63
FEATURE                  Location/Qualifiers
source                   1..63
                         mol_type = protein
                         organism = synthetic construct
SEQUENCE: 56
WWGDIWWKTM MELRSLDTQK ATCHLQQVTD LPWTSVSSPV EREILYHTVA RTKISDDDDE    60
HTL                                                                 63

SEQ ID NO: 57            moltype = AA   length = 25
FEATURE                  Location/Qualifiers
source                   1..25
                         mol_type = protein
                         organism = synthetic construct
SEQUENCE: 57
RKRTRERASR ASTWEGRRRL NTQTL                                         25

SEQ ID NO: 58            moltype = AA   length = 88
FEATURE                  Location/Qualifiers
source                   1..88
                         mol_type = protein
                         organism = synthetic construct
SEQUENCE: 58
WFLKRERQEE YIEEKKRVDI CRETPNICPH SGENTEYDTI PHTNRTILKE DPANTVYSTV    60
EIPKKMENPH SLLTMPDTPR LFAYENVI                                      88

SEQ ID NO: 59            moltype = AA   length = 42
FEATURE                  Location/Qualifiers
source                   1..42
                         mol_type = protein
                         organism = synthetic construct
SEQUENCE: 59
GVLLLSLVIT LYCNHRNRRR VCKCPRPVVK SGDKPSLSAR YV                       42

SEQ ID NO: 60            moltype = AA   length = 549
FEATURE                  Location/Qualifiers
source                   1..549
                         mol_type = protein
                         organism = synthetic construct
SEQUENCE: 60
SNLFVASWIA VMIIFRIGMA VAIFCCFFFP SWRRKRKEKQ SETSPKEFLT IYEDVKDLKT    60
RRNHEQEQTF PGGGSTIYSM IQSQSSAPTS QEPAYTLYSL IQPSRKSGSR KRNHSPSFNS   120
TIYEVIGKSQ PKAQNPARLS RKELENFDVY SNCRNTGPWL KKVLKCNTPD PSKFFSQLSS   180
EHGGDVQKWL SSPFPSSSFS PGGLAPEISP LEVLERDKVT QLLLQQDKVP EPASLSSNHS   240
LTSCFTNQGY FFFHLPDALE IEACQVYFTY DPYSEEDPDE GVAGAPTGSS PQPLQPLSGE   300
DDAYCTFPSR DDLLLFSPSL LGGPSPPSTA PGGSGAGEER MPPSLQERVP RDWDPQPLGE   360
PTPGVPDLVD FQPPPELVLR EAGEEVPDAG PREGVSFPWS RPPGQGEFRA LNARLPLNTD   420
AYLSLQELQG QDPTHLVRVK FSRSADAPAY QQGQNQLYNE LNLGRREEYD VLDKRRGRDP   480
EMGGKPRRKN PQEGLYNELQ KDKMAEAYSE IGMKGERRRG KGHDGLYQGL STATKDTYDA   540
LHMQALPPR                                                          549

SEQ ID NO: 61            moltype = AA   length = 178
FEATURE                  Location/Qualifiers
source                   1..178
                         mol_type = protein
                         organism = synthetic construct
SEQUENCE: 61
IYIWAPLAGT CGVLLLSLVI TLYCKRGRKK LLYIFKQPFM RPVQTTQEED GCSCRFPEEE    60
EGGCELRVKF SRSADAPAYQ QGQNQLYNEL NLGRREEYDV LDKRRGRDPE MGGKPRRKNP   120
QEGLFNELQK DKMAEAFSEI GMKGERRRGK GHDGLFQGLS TATKDTFDAL HMQALPPR     178

SEQ ID NO: 62            moltype = AA   length = 300
FEATURE                  Location/Qualifiers
source                   1..300
                         mol_type = protein
                         organism = synthetic construct
SEQUENCE: 62
FWVLVVGGV LACYSLLVTV AFIIFWVRSK RSRLLHSDYM NMTPRRPGPT RKHYQPYAPP     60
RDFAAYRSWR RKRKEKQSET SPKEFLTIYE DVKDLKTRRN HEQEQTFPGG GSTIYSMIQS   120
QSSAPTSQEP AYTLYSLIQP SRKSGSRKRN HSPSFNSTIY EVIGKSQPKA QNPARLSRKE   180
```

```
LENFDVYSRV KFSRSADAPA YQQGQNQLYN ELNLGRREEY DVLDKRRGRD PEMGGKPRRK    240
NPQEGLYNEL QKDKMAEAYS EIGMKGERRR GKGHDGLYQG LSTATKDTYD ALHMQALPPR    300

SEQ ID NO: 63           moltype = AA   length = 180
FEATURE                 Location/Qualifiers
source                  1..180
                        mol_type = protein
                        organism = synthetic construct
SEQUENCE: 63
FWVLVVVGGV LACYSLLVTV AFIIFWVRSK RSRLLHSDYM NMTPRRPGPT RKHYQPYAPP    60
RDFAAYRSRV KFSRSADAPA YQQGQNQLYN ELNLGRREEY DVLDKRRGRD PEMGGKPRRK    120
NPQEGLFNEL QKDKMAEAFS EIGMKGERRR GKGHDGLFQG LSTATKDTFD ALHMQALPPR    180

SEQ ID NO: 64           moltype = AA   length = 244
FEATURE                 Location/Qualifiers
source                  1..244
                        mol_type = protein
                        organism = synthetic construct
SEQUENCE: 64
FLFVLLGVGS MGVAAIVWGA WFWGRRSCQQ RDSGNSPGNA FYSNVLYRPR GAPKKSEDCS    60
GEGKDQRGQS IYSTSFPQPA PRQPHLASRP CPSPRPCPSP RPGHPVSMVR VSPRPSPTQQ    120
PRPKGFPKVG EERVKFSRSA DAPAYQQGQN QLYNELNLGR REEYDVLDKR RGRDPEMGGK    180
PRRKNPQEGL YNELQKDKMA EAYSEIGMKG ERRRGKGHDG LYQGLSTATK DTYDALHMQA    240
LPPR                                                                244

SEQ ID NO: 65           moltype = AA   length = 194
FEATURE                 Location/Qualifiers
source                  1..194
                        mol_type = protein
                        organism = synthetic construct
SEQUENCE: 65
GGTVLLLLFV ISITTIIVIF LNRRRRRERR DLFTESWDTQ KAPNNYRSPI STSQPTNQSM    60
DDTREDIYVN YPTFSRRPKT RVRVKFSRSA DAPAYQQGQN QLYNELNLGR REEYDVLDKR    120
RGRDPEMGGK PRRKNPQEGL YNELQKDKMA EAYSEIGMKG ERRRGKGHDG LYQGLSTATK    180
DTYDALHMQA LPPR                                                     194

SEQ ID NO: 66           moltype = AA   length = 186
FEATURE                 Location/Qualifiers
source                  1..186
                        mol_type = protein
                        organism = synthetic construct
SEQUENCE: 66
TTPGERSSLP AFYPGTSGSC SGCGSLSLPL LAGLVAADAV ASLLIVGAVF LCARPRRSPA    60
QEDGKVYINM PGRGRVKFSR SADAPAYQQG QNQLYNELNL GRREEYDVLD KRRGRDPEMG    120
GKPRRKNPQE GLYNELQKDK MAEAYSEIGM KGERRRGKGH DGLYQGLSTA TKDTYDALHM    180
QALPPR                                                              186

SEQ ID NO: 67           moltype = AA   length = 171
FEATURE                 Location/Qualifiers
source                  1..171
                        mol_type = protein
                        organism = synthetic construct
SEQUENCE: 67
VLIGTSVVKI PFTILLFFLL HRWCSNKKNA AVMDQEPAGN RTVNSEDSDE QDHQEVSYAR    60
VKFSRSADAP AYQQGQNQLY NELNLGRREE YDVLDKRRGR DPEMGGKPRR KNPQEGLYNE    120
LQKDKMAEAY SEIGMKGERR RGKGHDGLYQ GLSTATKDTY DALHMQALPP R             171

SEQ ID NO: 68           moltype = AA   length = 83
FEATURE                 Location/Qualifiers
source                  1..83
                        mol_type = protein
                        organism = synthetic construct
SEQUENCE: 68
VLIGTSVVKI PFTILLFFLL HRWCSNKKNA AVMDQEPAGN RTVNSEDSDE QDHQEVSYAL    60
CARPRRSPAQ EDGKVYINMP GRG                                           83

SEQ ID NO: 69           moltype = AA   length = 179
FEATURE                 Location/Qualifiers
source                  1..179
                        mol_type = protein
                        organism = synthetic construct
SEQUENCE: 69
VLIGTSVVKI PFTILLFFLL HRWCSNKKNA AVMDQEPAGN RTVNSEDSDE QDHQEVSYAW    60
RRKRKEKQSE TSPKEFLTIY EDVKDLKTRR NHEQEQTFPG GGSTIYSMIQ SQSSAPTSQE    120
PAYTLYSLIQ PSRKSGSRKR NHSPSFNSTI YEVIGKSQPK AQNPARLSRK ELENFDVYS    179

SEQ ID NO: 70           moltype = AA   length = 190
FEATURE                 Location/Qualifiers
source                  1..190
```

```
                        mol_type = protein
                        organism = synthetic construct
SEQUENCE: 70
VSFCLVMVLL FAVDTGLYFS VKTNIRSSTR DWKDHKFKWR KDPQDKWRRK RKEKQSETSP    60
KEFLTIYEDV KDLKTRRNHE QEQTFPGGGS TIYSMIQSQS SAPTSQEPAY TLYSLIQPSR   120
KSGSRKRNHS PSFNSTIYEV IGKSQPKAQN PARLSRKELE NFDVYSLCAR PRRSPAQEDG   180
KVYINMPGRG                                                         190

SEQ ID NO: 71           moltype = AA   length = 107
FEATURE                 Location/Qualifiers
source                  1..107
                        mol_type = protein
                        organism = synthetic construct
SEQUENCE: 71
VSFCLVMVLL FAVDTGLYFS VKTNIRSSTR DWKDHKFKWR KDPQDKNRRR RRERRDLFTE    60
SWDTQKAPNN YRSPISTSQP TNQSMDDTRE DIYVNYPTFS RRPKTRV                 107

SEQ ID NO: 72           moltype = AA   length = 166
FEATURE                 Location/Qualifiers
source                  1..166
                        mol_type = protein
                        organism = synthetic construct
SEQUENCE: 72
MGLAFLVLVA LVWFLVEDWL SRKRTRERAS RASTWEGRRR LNTQTLWRRK RKEKQSETSP    60
KEFLTIYEDV KDLKTRRNHE QEQTFPGGGS TIYSMIQSQS SAPTSQEPAY TLYSLIQPSR   120
KSGSRKRNHS PSFNSTIYEV IGKSQPKAQN PARLSRKELE NFDVYS                 166

SEQ ID NO: 73           moltype = AA   length = 278
FEATURE                 Location/Qualifiers
source                  1..278
                        mol_type = protein
                        organism = synthetic construct
SEQUENCE: 73
MGLAFLVLVA LVWFLVEDWL SRKRTRERAS RASTWEGRRR LNTQTLWRRK RKEKQSETSP    60
KEFLTIYEDV KDLKTRRNHE QEQTFPGGGS TIYSMIQSQS SAPTSQEPAY TLYSLIQPSR   120
KSGSRKRNHS PSFNSTIYEV IGKSQPKAQN PARLSRKELE NFDVYSRVKF SRSADAPAYQ   180
QGQNQLYNEL NLGRREEYDV LDKRRGRDPE MGGKPRRKNP QEGLYNELQK DKMAEAYSEI   240
GMKGERRRGK GHDGLYQGLS TATKDTYDAL HMQALPPR                          278

SEQ ID NO: 74           moltype = AA   length = 186
FEATURE                 Location/Qualifiers
source                  1..186
                        mol_type = protein
                        organism = synthetic construct
SEQUENCE: 74
MGLAFLVLVA LVWFLVEDWL SRKRTRERAS RASTWEGRRR LNTQTLKRKK QRSRRNDEEL    60
ETRAHRVATE ERGRKPHQIP ASTPQNPATS QHPPPPPGHR SQAPSHRPPP PGHRVQHQPQ   120
KRPPAPSGTQ VHQQKGPPLP RPRVQPKPPH GAAENSLSPS SNLCARPRRS PAQEDGKVYI   180
NMPGRG                                                             186

SEQ ID NO: 75           moltype = AA   length = 254
FEATURE                 Location/Qualifiers
source                  1..254
                        mol_type = protein
                        organism = synthetic construct
SEQUENCE: 75
IYLIIGICGG GSLLMVFVAL LVFYITKRKK QRSRRNDEEL ETRAHRVATE ERGRKPHQIP    60
ASTPQNPATS QHPPPPPGHR SQAPSHRPPP PGHRVQHQPQ KRPPAPSGTQ VHQQKGPPLP   120
RPRVQPKPPH GAAENSLSPS SNRVKFSRSA DAPAYQQGQN QLYNELNLGR REEYDVLDKR   180
RGRDPEMGGK PRRKNPQEGL YNELQKDKMA EAYSEIGMKG ERRRGKGHDG LYQGLSTATK   240
DTYDALHMQA LPPR                                                    254

SEQ ID NO: 76           moltype = AA   length = 253
FEATURE                 Location/Qualifiers
source                  1..253
                        mol_type = protein
                        organism = synthetic construct
SEQUENCE: 76
FLVIIVILSA LFLGTLACFC VWRRKRKEKQ SETSPKEFLT IYEDVKDLKT RRNHEQEQTF    60
PGGGSTIYSM IQSQSSAPTS QEPAYTLYSL IQPSRKSGSR KRNHSPSFNS TIYEVIGKSQ   120
PKAQNPARLS RKELENFDVY SRVKFSRSAD APAYQQGQNQ LYNELNLGRR EEYDVLDKRR   180
GRDPEMGGKP RRKNPQEGLY NELQKDKMAE AYSEIGMKGE RRRGKGHDGL YQGLSTATKD   240
TYDALHMQAL PPR                                                     253

SEQ ID NO: 77           moltype = AA   length = 183
FEATURE                 Location/Qualifiers
source                  1..183
                        mol_type = protein
                        organism = synthetic construct
```

```
SEQUENCE: 77
FLVIIVILSA LFLGTLACFC VWRRKRKEKQ SETSPKEFLT IYEDVKDLKT RRNHEQEQTF    60
PGGGSTIYSM IQSQSSAPTS QEPAYTLYSL IQPSRKSGSR KRNHSPSFNS TIYEVIGKSQ   120
PKAQNPARLS RKELENFDVY SRLKIQVRKA AITSYEKSDG VYTGLSTRNQ ETYETLKHEK   180
PPQ                                                                183

SEQ ID NO: 78           moltype = AA   length = 221
FEATURE                 Location/Qualifiers
source                  1..221
                        mol_type = protein
                        organism = synthetic construct
SEQUENCE: 78
VLLCLLLVPL LLSLFVLGLF LWFLKRERQE EYIEEKKRVD ICRETPNICP HSGENTEYDT    60
IPHTNRTILK EDPANTVYST VEIPKKMENP HSLLTMPDTP RLFAYENVIR VKFSRSADAP   120
AYQQGQNQLY NELNLGRREE YDVLDKRRGR DPEMGGKPRR KNPQEGLYNE LQKDKMAEAY   180
SEIGMKGERR RGKGHDGLYQ GLSTATKDTY DALHMQALPP R                      221

SEQ ID NO: 79           moltype = AA   length = 18
FEATURE                 Location/Qualifiers
source                  1..18
                        mol_type = protein
                        organism = synthetic construct
SEQUENCE: 79
MALPVTALLL PLALLLHA                                                 18

SEQ ID NO: 80           moltype = AA   length = 21
FEATURE                 Location/Qualifiers
source                  1..21
                        mol_type = protein
                        organism = synthetic construct
SEQUENCE: 80
MDFQVQIFSF LLISASVIMS R                                             21

SEQ ID NO: 81           moltype = AA   length = 39
FEATURE                 Location/Qualifiers
source                  1..39
                        mol_type = protein
                        organism = synthetic construct
SEQUENCE: 81
IEVMYPPPYL DNEKSNGTII HVKGKHLCPS PLFPGPSKP                          39

SEQ ID NO: 82           moltype = AA   length = 88
FEATURE                 Location/Qualifiers
source                  1..88
                        mol_type = protein
                        organism = synthetic construct
SEQUENCE: 82
ESKYGPPCPP CPGGGSSGGG SGGQPREPQV YTLPPSQEEM TKNQVSLTCL VKGFYPSDIA    60
VEWESNGQPE NNYKTTPPVL DSDGSFFL                                      88

SEQ ID NO: 83           moltype = AA   length = 89
FEATURE                 Location/Qualifiers
source                  1..89
                        mol_type = protein
                        organism = synthetic construct
SEQUENCE: 83
ESKYGPPCPP CPAPEFEGGP SVFLFPPKPK DTLMISRTPE VTCVVVDVSQ EDPEVQFNWY    60
VDGVEVHNAK TKPREEQFQS TYRVVSVLT                                     89

SEQ ID NO: 84           moltype = AA   length = 129
FEATURE                 Location/Qualifiers
source                  1..129
                        mol_type = protein
                        organism = synthetic construct
SEQUENCE: 84
ESKYGPPCPP CPGGGSSGGG SGGQPREPQV YTLPPSQEEM TKNQVSLTCL VKGFYPSDIA    60
VEWESNGQPE NNYKTTPPVL DSDGSFFLYS RLTVDKSRWQ EGNVFSCSVM HEALHNHYTQ   120
KSLSLSLGK                                                          129

SEQ ID NO: 85           moltype = AA   length = 229
FEATURE                 Location/Qualifiers
source                  1..229
                        mol_type = protein
                        organism = synthetic construct
SEQUENCE: 85
ESKYGPPCPP CPAPEFEGGP SVFLFPPKPK DTLMISRTPE VTCVVVDVSQ EDPEVQFNWY    60
VDGVEVHNAK TKPREEQFQS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGK               229
```

```
SEQ ID NO: 86              moltype = AA  length = 310
FEATURE                    Location/Qualifiers
source                     1..310
                           mol_type = protein
                           organism = synthetic construct
SEQUENCE: 86
ESKYGPPCPP  CPGGGSSGGG  SGGQPREPQV  YTLPPSQEEM  TKNQVSLTCL  VKGFYPSDIA   60
VEWESNGQPE  NNYKTTPPVL  DSDGSFFLYS  RLTVDKSRWQ  EGNVFSCSVM  HEALHNHYTQ  120
KSLSLSLGKM  FWVLVVVGGV  LACYSLLVTV  AFIIFWVRSK  RSRLLHSDYM  NMTPRRPGPT  180
RKHYQPYAPP  RDFAAYRSRV  KFSRSADAPA  YQQGQNQLYN  ELNLGRREEY  DVLDKRRGRD  240
PEMGGKPRRK  NPQEGLFNEL  QKDKMAEAFS  EIGMKGERRR  GKGHDGLFQG  LSTATKDTFD  300
ALHMQALPPR                                                              310

SEQ ID NO: 87              moltype = AA  length = 263
FEATURE                    Location/Qualifiers
source                     1..263
                           mol_type = protein
                           organism = synthetic construct
SEQUENCE: 87
SNLFVASWIA  VMIIFRIGMA  VAIFCCFFFP  SWRRKRKEKQ  SETSPKEFLT  IYEDVKDLKT   60
RRNHEQEQTF  PGGGSTIYSM  IQSQSSAPTS  QEPAYTLYSL  IQPSRKSGSR  KRNHSPSFNS  120
TIYEVIGKSQ  PKAQNPARLS  RKELENFDVY  SRVKFSRSAD  APAYKQGQNQ  LYNELNLGRR  180
EEYDVLDKRR  GRDPEMGGKP  RRKNPQEGLY  NELQKDKMAE  AYSEIGMKGE  RRRGKGHDGL  240
YQGLSTATKD  TYDALHMQAL  PPR                                             263

SEQ ID NO: 88              moltype = AA  length = 556
FEATURE                    Location/Qualifiers
source                     1..556
                           mol_type = protein
                           organism = synthetic construct
SEQUENCE: 88
EVQLVESGGG  LVQPGGSLKL  SCAASGFTFS  NYGMSWVRQT  PDRRLELVAT  INNNGGGTYY   60
PDSVKGRFTI  SRDNAKNTLY  LQMSSLKSED  TAMYYCTSPG  LLWDAWGAGT  TVTVSSGSTS  120
GGGSGGGSGG  GGSSDVVMTQ  TPLTLSVSIG  QPASISCKSS  QSLLDSDGRT  YLNWLLQRPG  180
QSPKRLIYLV  SKLDSGAPDR  FTGSGSGTDF  TLKISRVEAE  DLGVYYCWQG  THFPQTFGGG  240
TKLEIKESKY  GPPCPPCPGG  GSSGGGSGGQ  PREPQVYTLP  PSQEEMTKNQ  VSLTCLVKGF  300
YPSDIAVEWE  SNGQPENNYK  TTPPVLDSDG  SFFLYSRLTV  DKSRWQEGNV  FSCSVMHEAL  360
HNHYTQKSLS  LSLGKMFWVL  VVVGGVLACY  SLLVTVAFII  FWVRSKRSRL  LHSDYMNMTP  420
RRPGPTRKHY  QPYAPPRDFA  AYRSRVKFSR  SADAPAYQQG  QNQLYNELNL  GRREEYDVLD  480
KRRGRDPEMG  GKPRRKNPQE  GLFNELQKDK  MAEAFSEIGM  KGERRRGKGH  DGLFQGLSTA  540
TKDTFDALHM  QALPPR                                                      556

SEQ ID NO: 89              moltype = AA  length = 121
FEATURE                    Location/Qualifiers
source                     1..121
                           mol_type = protein
                           organism = synthetic construct
SEQUENCE: 89
QVTLKESGPG  ILQPSQTLSL  TCSFSGFSLS  TSGMGVSWIR  QPSGKGLEWL  AHIFWDDDKR   60
YNPSLKSRLT  ISKDTSRNKV  FLKITSVDTA  DTATYYCARR  VVATDWYFDV  WGAGTTVTVS  120
S                                                                       121

SEQ ID NO: 90              moltype = AA  length = 110
FEATURE                    Location/Qualifiers
source                     1..110
                           mol_type = protein
                           organism = synthetic construct
SEQUENCE: 90
DIVLTQSPAS  LAVSLGQRAT  ISCRASESVE  YYGTTLMQWY  QQKPGQPPKL  LIYAASKVES   60
GVPARFSGSG  SGTDFSLNIH  PVEEDDVAMY  FCQQSRKVPL  TFGAGTKLEL              110
```